United States Patent
Hua et al.

(10) Patent No.: US 10,598,658 B2
(45) Date of Patent: Mar. 24, 2020

(54) REDUCED GRAPHENE OXIDE-BASED BIOSENSOR AND USE THEREOF

(71) Applicant: Chang Gung University, Taoyuan (TW)

(72) Inventors: Mu-Yi Hua, Taoyuan (TW); Hsiao-Chien Chen, Taichung (TW); Yi-Ting Chen, Taoyuan (TW); Rung-Ywan Tsai, Hsinchu County (TW); Min-Cheng Chen, Hsinchu (TW); Chien-Lun Chen, New Taipei (TW)

(73) Assignee: Chang Gung University, Taoyuan (TW)

( * ) Notice: Subject to any disclaimer, the term of this patent is extended or adjusted under 35 U.S.C. 154(b) by 710 days.

(21) Appl. No.: 14/942,378

(22) Filed: Nov. 16, 2015

(65) Prior Publication Data

US 2016/0334399 A1  Nov. 17, 2016

(30) Foreign Application Priority Data

May 14, 2015 (TW) .............................. 104115392 A

(51) Int. Cl.
*G01N 27/414* (2006.01)
*G01N 33/543* (2006.01)

(52) U.S. Cl.
CPC ... *G01N 33/54393* (2013.01); *G01N 27/4145* (2013.01); *G01N 27/4146* (2013.01); *G01N 33/5438* (2013.01); *G01N 33/54353* (2013.01); *G01N 2333/775* (2013.01)

(58) Field of Classification Search
CPC ............................ G01N 27/414; G01N 33/543
See application file for complete search history.

(56) References Cited

U.S. PATENT DOCUMENTS

2013/0137894 A1* 5/2013 Hua ........................ C07C 59/76
562/488

OTHER PUBLICATIONS

Chang et al., "Ultrasonic-assisted self-assembly of monolayer graphene oxide for rapid detection of *Escherichia coli*", Nanoscale, 2013, vol. 5, pp. 3620-3626, published Mar. 6, 2013 (Year: 2013).*
Yi-Ting et al., "Multiplexed quantification of 63 proteins in human urine by multiple reaction monitoring-based mass spectrometry for discovery of potential bladder cancer biomarkers", Journal of Proteomics, vol. 75, pp. 3529-3545, published on Jan. 3, 2012. (Year: 2012).*
Chen et al., "Magnetic-Composite-Modified Polycrystalline Silicon Nanowire Field-Effect Transistor for Vascular Endothelial Growth Factor Detection and Cancer Diagnosis" Anal. Chem., (2014), vol. 86, pp. 9443-9450, published on Mar. 19, 2014). (Year: 2014).*
Xue et al. ("Oxidizing metal ions with graphene oxide: the in situ formation of magnetic nanoparticles on self-reduced graphene sheets for multifunctional application", Chem. Commun., vol. 47, pp. 11689-11691, published Sep. 26, 2011) (Year: 2011).*
Liu et al. ("Carbon nanomaterials field-effect-transistor-based biosensors", NPG Asia Materials, vol. 4 (e23), pp. 1-10, published Aug. 17, 2012) (Year: 2012).*
Hsiao-Chien Chen, et al., "A sensitive and selective magnetic graphene composite-modified polycrystalline-silicon nanowire field-effect transistor for bladder cancer diagnosis", Biosensors and Bioelectronics 66 (2015), pp. 198-207.

* cited by examiner

*Primary Examiner* — Tracy Vivlemore
*Assistant Examiner* — Nam P Nguyen
(74) *Attorney, Agent, or Firm* — Cesari and McKenna, LLP

(57) ABSTRACT

A reduced graphene oxide-based biosensor includes a nanostructure field-effect transistor including a channel region which includes a reduced graphene oxide having a linking moiety to be bonded to a receptor specific to an analyte, and which is represented by a formula of —(C=O)—X—COOH, wherein X represents a C1-C3 alkenylene group or a C1-C3 alkylene group.

11 Claims, 19 Drawing Sheets

GLA13　　　MGLA

REDUCED GRAPHENE OXIDE-BASED BIOSENSOR AND USE THEREOF

CROSS-REFERENCE TO RELATED APPLICATIONS

This application claims priority of Taiwanese Application No. 104115392, filed on May 14, 2015.

BACKGROUND

Field

The disclosure relates to a biosensor, and more particularly to a reduced graphene oxide-based biosensor. The disclosure also relates to a method for detecting an analyte using the biosensor.

Background Information

Recently, biosensors have been used widely for diagnosis of various diseases. In particular, nano-scaled biosensors, such as nanowire field effect transistor (FET)-based biosensors, made from semiconductor nano materials have gained much attention due to their advantages, such as high sensitivity, high selectivity, and fast analysis.

Graphene sheets have a high surface area and superior conductivity, and thus are often used for modifying FET. However, as graphene sheets lack functional groups for the immobilization of biomolecules (for example, antibodies), it is difficult to directly use graphene sheets in FET-based biosensors. Therefore, recently more investigations have been focused on the modification of graphene sheets used in FET-based biosensors so as to promote the immobilization of biomolecules onto graphene sheets.

It has been disclosed in the art, for example, *Materials Chemistry and Physics*, vol. 136 (2012), p 304-308; and *Nanoscale*, 2013, vol. 5, p 3620-3626, to modify the graphene sheets used for FETs using the Hummers' method so as to obtain a modified graphene sheet including short-chain carboxylic groups each having one carbon atom. Each of the short-chain carboxylic groups included in the modified graphene sheet is used for bonding a receptor specific to an analyte so as to produce a FET-based biosensor. However, the amount and the bioactivity of the receptors contained in the biosensor thus produced are relatively low due to the fact that the chain length of the short-chain carboxylic groups is relatively short.

There is a need in the art for a biosensor with receptors that are higher in amount and bioactivity of receptors as compared to the aforesaid biosensor which is produced from a graphene sheet modified by the Hummers' method.

SUMMARY

Therefore, an object of the disclosure is to provide a reduced graphene oxide-based biosensor having receptors in an increased amount and with enhanced bioactivity.

Another object of the disclosure is to provide a method for detecting an analyte using the reduced graphene oxide-based biosensor.

A reduced graphene oxide-based biosensor according to a first aspect of the disclosure includes a nano-structure field-effect transistor including a channel region which includes a reduced graphene oxide having a linking moiety to be bonded to a receptor specific to an analyte, and which is represented by a formula of —(C═O)—X—COOH, wherein X represents a $C_1$-$C_3$ alkenylene group or a $C_1$-$C_3$ alkylene group.

A method for detecting an analyte according to a second aspect of the disclosure includes the steps of:

applying a predetermined potential to the channel region through a gate electrode of the reduced graphene oxide-based biosensor of the disclosure;

bringing the reduced graphene oxide-based biosensor into contact with the analyte; and measuring a change in current of the reduced graphene oxide-based biosensor before and after the reduced graphene oxide-based biosensor is brought into contact with the analyte for determining a concentration of the analyte.

In the reduced graphene oxide-based biosensor of the disclosure, the linking moiety (i.e., —(C═O)—X—COOH) for immobilizing a receptor specific to an analyte to the reduced graphene oxide included in the channel region has a relatively large chain length (i.e., a higher carbon number) and more freedom compared to the short-chain carboxylic groups in the aforesaid prior art, thereby preventing steric hindrance during the immobilization of the receptor and increasing the amount of the immobilized receptor. In addition, the linking moiety having a relatively large long chain may extend and bend at random angles to produce a relatively large space for targeting the analyte, resulting in higher bioactivity of the receptor. Therefore, the reduced graphene oxide-based biosensor of the disclosure has enhanced sensitivity.

BRIEF DESCRIPTION OF THE DRAWINGS

Other features and advantages of the disclosure will become apparent in the following detailed description of the embodiments with reference to the accompanying drawing, of which.

DETAILED DESCRIPTION

Figure 1:
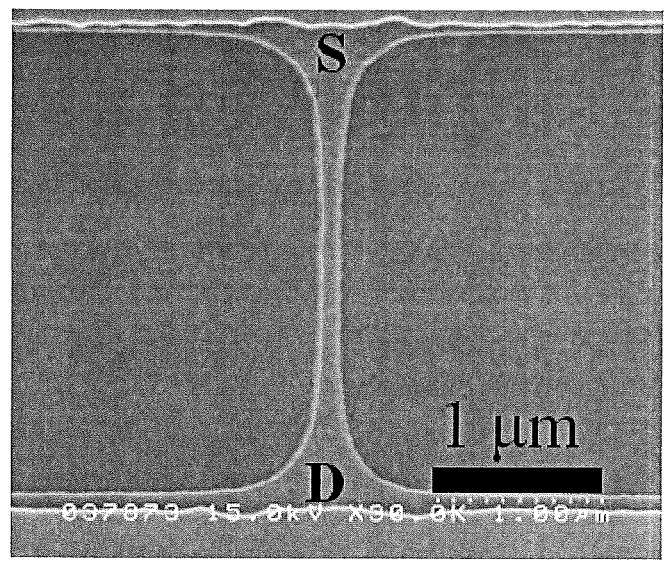
FIG. 1 is a scanning electron microscope (SEM) image illustrating a microscopic structure of an N-type polycrystalline silicon nanowire field effect transistor used in a biosensor of Example 1.

Biosensor:

A reduced graphene oxide-based biosensor according to a first aspect of the disclosure includes a nano-structure field-effect transistor including a channel region which includes a reduced graphene oxide having a linking moiety to be bonded to a receptor specific to an analyte, and which is represented by a formula of —(C=O)—X—COOH, wherein X represents a $C_1$-$C_3$ alkenylene group or a $C_1$-$C_3$ alkylene group. Preferably, X is a $C_1$-$C_3$ alkenylene group. More preferably, X is a vinylene group.

Preferably, the nano-structure field-effect transistor is a nanowire field-effect transistor. More preferably, the nano-structure field-effect transistor is a polycrystalline silicon nanowire field-effect transistor (referred to as poly-SiNW-FET hereinafter). The nano-structure field-effect transistor used in the illustrated examples is an n-type poly-SiNW-FET.

The channel region further includes at least one magnetic nanoparticle which is combined with the reduced graphene oxide to form a composite. Preferably, the composite has a size ranging from 30 nm to 50 nm.

The channel region further includes an immobilization layer for immobilizing the composite. Preferably, the immobilization layer is made by forming a self-assembled monolayer of an aminosilane compound in the channel region and subjecting a dialdehyde compound and the aminosilane compound to a reaction so as to attach an aldehyde group of the dialdehyde compound to the self-assembled monolayer for bonding to the composite.

Preferably, the aminosilane compound is (3-aminopropyl) triethoxysilane (referred to as APTES hereinafter), (3-aminopropyl) trimethoxysilane (referred to as APTMS hereinafter, or a combination thereof. The aminosilane compound used in the illustrated examples is APTES.

Preferably, the dialdehyde compound is glutaraldehyde (referred to as GA hereinafter), glyoxal, malonaldehyde, succinaldehyde, adipaldehyde, or combinations thereof. The dialdehyde compound used in the illustrated examples is GA.

Preferably, the receptor bonded to the linking moiety contained in the reduced graphene oxide is an antibody. More preferably, the antibody is an anti-apolipoprotein A II antibody (referred to as anti-APOA2 antibody hereinafter) for urinary quantification of apolipoprotein A II protein (referred to as APOA2 protein hereinafter), which is a biomarker for diagnosis of bladder cancer.

Preferably, the reduced graphene oxide having the linking moiety is prepared by subjecting a cyclic dianhydride compound and a graphite to a Friedel-Crafts reaction in the presence of a Lewis acid. Specifically, the Friedel-Crafts reaction is performed by contacting the cyclic dianhydride compound with the Lewis acid to form a ring-opened intermediate, and grafting the ring-opened intermediate to the graphene. The preparation of the reduced graphene oxide having the linking moiety is disclosed in detail in U.S. Patent Publication No. 2013/0137894, which is incorporated herein by reference.

The molar ratio of the Lewis acid (as a catalyst) to the cyclic dianhydride compound ranges preferably from 1 to 6 and more preferably from 2 to 4. Most preferably, the molar ratio of the Lewis acid to the cyclic dianhydride compound is 3. When the molar ratio of the Lewis acid to the cyclic dianhydride compound is more than 6, the viscosity of a reaction solution is increased due to the fact that excess Lewis acid hinders reactive collisions, and the reduced graphene oxide thus formed may have a relatively small amount of the linking moiety (i.e., —(C=O)—X—COOH). When the molar ratio of the Lewis acid to the cyclic dianhydride compound is less than 1, the ring-opening reaction may be negatively affected due to an insufficient amount of the Lewis acid, and the reduced graphene oxide thus formed may also have a relatively small amount of the linking moiety.

Preferably, the cyclic dianhydride compound is maleic anhydride (referred to as MA hereinafter), succinic anhydride, or a combination thereof.

It should be noted that the linking moiety (i.e., —(C=O)—X—COOH) contained in the reduced graphene oxide is first reacted with N-hydroxysulfo-succinimide sodium salt (referred to as sulfo-NHS hereinafter) and 1-ethyl-3-(3-dimethylaminopropyl)carbodiimide (referred to as EDC hereinafter), and then with the antibody so as to bond the antibody to the linking moiety.

The magnetic nanoparticle contained in the composite may accelerate purification during the immobilization of the antibody, thus preventing denaturation of the antibody.

Preferably, the magnetic nanoparticle is a $Fe_3O_4$ magnetic nanoparticle, a Ni magnetic nanoparticle, or a combination thereof. The magnetic nanoparticle used in the illustrated examples is the $Fe_3O_4$ magnetic nanoparticle.

The magnetic nanoparticle has an average particle diameter ranging preferably from 4 to 50 nm and more preferably from 4 to 10 nm.

Preparation of a Biosensor:

The biosensor of the disclosure is prepared by the steps of:

forming the immobilization layer in the channel region of the nano-structure field-effect transistor;

forming a detecting unit by the sub-steps of: forming the reduced graphene oxide having the linking moiety (i.e., —(C=O)—X—COOH), combining the reduced graphene oxide with the magnetic nanoparticle to form a composite, and bonding the antibody to the linking moiety; and immobilizing the detecting unit to the immobilization layer.

The following examples are provided to illustrate the embodiments of the disclosure, and should not be construed as limiting the scope of the disclosure.

EXAMPLES

Sources of Chemicals:

| Chemicals | Sources |
| --- | --- |
| Graphite: | Alfa Aesar |
| Maleic anhydride (MA): | TCI |
| (sulfo-NHS) | Fluka |
| phosphate buffered saline (PBS): | Sigma |
| EDC: | Sigma |
| bovine serum albumin (BSA): | Sigma |
| MES buffer solution (pH = 6.3): | Sigma |
| Acetone: | Tedia |
| Methanol: | Tedia |
| N-methyl-2-pyrrolidone (NMP): | Tedia |
| Aluminum chloride ($AlCl_3$): | Acros |
| toluidine blue O (TBO): | Acros |
| Sodium hydroxide (NaOH): | Merck |
| Ferrous chloride ($FeCl_2$): | Merck |
| Ferric chloride ($FeCl_3$): | Merck |
| anti-APOA2 antibody: | Abcam, CB, UK |
| APOA2 protein: | Abcam, CB, UK |
| APTES: | Sigma |
| GA: | Sigma |
| Sodium nitrate: | Sigma |
| Potassium permanganate: | Sigma |
| Hydrogen peroxide: | Showa |
| Hydrochloric acid: | Tedia |
| 3,3',5,5'-Tetramethylbenzidine (TMB): | Sigma |

Preparation Examples 1-3

Preparation of Reduced Graphene Oxide having a Linking Moiety of —(C=O)—CH=CH—COOH (Referred to as GLA hereinafter)

Each of GLA11, GLA13, and GLA16 of Preparation Examples 1-3 was prepared using $AlCl_3$ and MA according to the following steps.

Step 1: Graphite (50 mg) was temporarily dispersed in anhydrous NMP (10 ml) with sonication to prepare a graphite solution.

Step 2: MA (1 g) was dispersed in anhydrous NMP (40 ml) under a nitrogen atmosphere, and $AlCl_3$ was then added at a molar ratio shown in Table 1 below at 90° C., followed by stirring for 3 hours to prepare a reaction solution.

Step 3: The graphite solution prepared in step 1 was added to the reaction solution prepared in step 2, following by a reaction at 160° C. for 48 hours to prepare a coarse GLA solution.

Step 4: The coarse GLA solution obtained in step 3 was filtered through a 0.1-μm poly(vinylidene fluoride) (PVDF) membrane and washed with methanol and deionized (DI) water three times to obtain a filtrate. A yellow solution was collected after centrifugation of the filtrate at 3000 rpm. Finally, the yellow solution was filtered through a 0.1-μm PVDF membrane to obtain a product.

TABLE 1

| Prep. Exs. | $AlCl_3$/MA (mole/mole) | |
| --- | --- | --- |
| 1 | 1 | GLA11 |
| 2 | 3 | GLA13 |
| 3 | 6 | GLA16 |

Preparation Example 4

Preparation of a Composite (Referred to as MGLA):

Step 1: GLA13 (200 mg) obtained in Preparation Example 2 was dispersed in DI water (20 ml), followed by focused ultra-sonication at 4° C. for 24 hours to obtain an aqueous GLA13 solution.

Step 2: $FeCl_3$ (4.32 mmol) and $FeCl_2 \cdot 4H_2O$ (6.48 mmol) were dissolved in DI water (380 ml) at 27° C. to obtain an iron-containing solution.

Step 3: The aqueous GLA13 solution obtained in step 1 and the iron-containing solution obtained in step 2 were mixed under a nitrogen atmosphere to obtain a mixed solution. After heating the mixed solution slowly to 50° C., a NaOH solution (30 ml, 0.576 N) was slowly added over 20 minutes, resulting in a final temperature of 80° C. The reaction was then rapidly quenched on ice, and a HCl solution (0.1 N) was slowly added until a neutral pH was reached, thereby obtaining a coarse MGLA solution.

Step 4: Coarse MGLA was separated from the coarse MGLA solution obtained in step 3 via application of a magnetic field and then was washed with DI water several times to obtain a composite (MGLA).

Preparation Examples 5-10

Preparation of a Detecting Unit (Referred to as Ab-MGLA hereinafter):

Each of the detecting units (Ab-MGLAs) of Preparation Examples 5-10 was prepared using an anti-APOA2 antibody according to the following steps.

Step 1: MGLA obtained in Preparation Example 4 was added to DI water to prepare an aqueous MGLA solution in a concentration of 10 μg/ml.

Step 2: EDC (50 mg) and sulfo-NHS (60 mg) were dissolved in a MES buffer solution (5 ml, pH=6.3) in the dark to obtain a reaction solution.

Step 3: the aqueous MGLA solution (0.1 ml) obtained in step 1 and the reaction solution (0.2 ml) obtained in step 2 were mixed at 25° C. with shaking for 30 minutes in the dark. After separation by application of a magnetic field, a solid was obtained. The solid was washed with the MES buffer solution (0.8 ml) to obtain a MGLA-containing reaction precursor.

Step 4: the MGLA-containing reaction precursor obtained in step 3 was re-suspended in the MES buffer solution (0.2 ml), followed by mixing with the anti-APOA2 antibody in the amount shown in Table 2 below at 25° C. for 3 hours to obtain a coarse Ab-MGLA solution.

Step 5: Coarse Ab-MGLA was separated from the coarse Ab-MGLA solution via application of a magnetic field and washed with PBS to remove free anti-APOA2 antibody to obtain a detecting unit (Ab-MGLA).

TABLE 2

| Prep. Exs. | anti-APOA2 antibody (ng) |
| --- | --- |
| 5 | 10 |
| 6 | 25 |
| 7 | 50 |
| 8 | 100 |
| 9 | 150 |
| 10 | 200 |

Preparation Example 11

Preparation of n-type Poly-SiNW-FET

N-type poly-SiNW-FET was prepared from a standard 6-inch p-type wafer according to the following steps.

Step 1: An oxide ($SiO_2$) layer (30 nm) and a nitride ($SiN_x$) layer (50 nm) were deposited in sequence onto a silicon substrate as an insulating layer to prevent the reaction species on the surface of nanowire FET from penetrating into the substrate.

Step 2: A polycrystalline silicon layer (50 nm) was then deposited on the nitride layer via chemical vapor deposition.

Step 3: The polycrystalline silicon layer was patterned using a standard I-line stepper in a complementary metal-oxide-semiconductor (CMOS) process to form nanowires. Photoresist was trimmed using reactive plasma etching, followed by silicon etching, so as to reduce the dimensions of the nanowires to approximately 0.3 μm.

Step 4: A pattern of channel protection photoresist was then formed via I-line lithography Channel protection photoresist patterning was performed to prevent the channel from intrinsically implanting $N^+$ source/drain (S/D) and to increase the field sensitivity of the nanowires.

Step 5: $N^+$ S/D was subsequently implanted using a $10^{15}$ $cm^{-2}$ $P_{31}^+$ ion beam (10 keV) into the nanowires to reduce the parasitic resistance of the nanowires.

Step 6: The channel protection photoresist was removed. S/D was activated by annealing at 600° C. for 30 minutes under a nitrogen atmosphere.

Step 7: A $SiN_x$ passivation layer was deposited onto the FET to protect a Si substrate gate from being damaged by the solutions used during pH testing, thereby obtaining the n-type poly-SiNW-FET.

FIG. 1 is a SEM image illustrating a microscopic structure of the n-type poly-SiNW-FET produced by the aforesaid method. As shown, the nanowire (i.e., the channel) of the poly-SiNW-FET thus produced has a length of 2 μm and a width of 0.15 μm.

Examples 1-4

Preparation of Biosensors (Ab-MGLA/Poly-SiNW-FET):

Each of the biosensors of Examples 1-4 was produced using the detecting unit (Ab-MGLA) of Preparation Example 8 in PBS (as a solvent) according to the following steps.

Step 1: A solution of 2 wt % APTES in ethanol (5) was placed on the poly-SiNW-FET prepared in Preparation Example 11 for 1 hour to form a self-assembled monolayer so as to functionally modify the poly-SiNW-FET with terminal amine groups.

Step 2: The poly-SiNW-FET modified in step 1 was then washed with ethanol and dried in an oven at 100° C. for 1 hour. The poly-SiNW-FET was further treated with an aqueous glutaraldehyde solution (5 wt %, 5 μl) for 1 hour. An immobilization layer having terminal aldehyde groups was formed in a channel region of poly-SiNW-FET.

Step 3: The poly-SiNW-FET obtained in step 2 was treated with a solution of Ab-MGLA in BPS (5 μl) of Preparation Example 8 in a concentration shown in Table 3 for 1 hour to immobilize Ab-MGLA to poly-SiNW-FET. Finally, a solution of BSA in PBS (5 μl, 5 mg/ml) was added at 4° C. for 1 hour in the dark to block non-specific binding, following by washing with PBS three times so as to obtain a biosensor (Ab-MGLA/poly-SiNW-FET).

TABLE 3

| Exs. | Concentrations of Ab-MGLA (µg/mL) |
| --- | --- |
| 1 | 0.025 |
| 2 | 0.125 |
| 3 | 0.625 |
| 4 | 1 |

Comparative Preparation Example 1

Preparation of Reduced Graphene Oxide having a Linking Moiety of —COOH (Referred to as GSA hereinafter)

GSA was synthesized using a method modified from the Hummers' method and including the following steps.

Step 1: Graphite (1 g) and sodium nitrate (0.5 g) were mixed. A concentrated sulfuric acid solution (23 ml, 95%) was added, followed by continuously stirring for 1 hour. Potassium permanganate (3 g) was slowly added at a temperature lower than 20° C., followed by stirring at 35° C. for 12 hours. Finally, water (500 ml) was added with vigorous stirring to obtain a coarse GSA solution.

Step 2: In order to ensure that the reaction with potassium permanganate was complete, a suspended substance in the coarse GSA solution obtained in step 1 was treated with hydrogen peroxide (30 wt %, 5 ml). The solid thus obtained was washed with hydrochloric acid and water, followed by filtration and drying to obtain GSA.

Comparative Preparation Example 2

Preparation of a Composite (Referred to as MGSA hereinafter)

The procedure of Preparation Example 4 was repeated except that GLA 13 used in Preparation Example 4 was replaced with GSA prepared in Comparative Preparation Example 1.

Comparative Preparation Examples 3-8

Preparation of Detecting Units (Referred to as Ab-MGSA hereinafter)

The procedure of Preparation Examples 5-10 was repeated for Comparative Preparation. Examples 3-8 except that the aqueous MGLA solution used in step 3 of Preparation Examples 5-10 was replaced with an aqueous MGSA solution (0.1 ml, 21.3 µg/ml). The amounts of the anti-APOA2 antibody used in Comparative Preparation Examples 3-8 are shown in Table 4 below.

TABLE 4

| Comp. Prep. Exs. | anti-APOA2 antibody (ng) |
| --- | --- |
| 3 | 10 |
| 4 | 25 |
| 5 | 50 |
| 6 | 100 |
| 7 | 150 |
| 8 | 200 |

Comparative Example 1

Preparation of a Biosensor (Ab-MGSA/Poly-SiNW-FET):

The procedure of Examples 1-4 was repeated for Comparative Example 1 except that the solution of Ab-MGLA in BPS used in step 3 was replaced with a solution of Ab-MGSA in BPS (5 µl, 21.3 µg/ml) obtained in Comparative Preparation Example 7.

Figure 2:
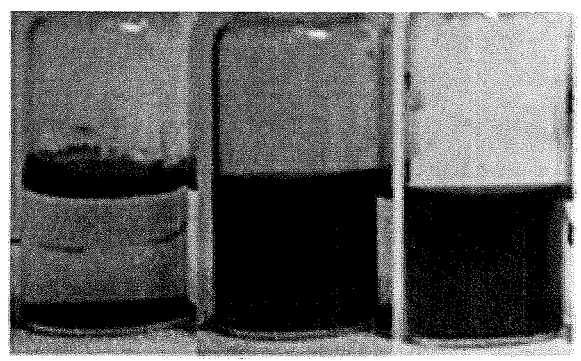
FIG. 2 is a photo illustrating a comparison of the solubilities of graphite, a modified graphene product (GLA13) of Preparation Example 1, and a modified graphene product (GSA) of Comparative Preparation Example 1 in water.

Test for Solubilities of Graphite, GLA, and GSA in Water:

The solubilities of graphite, GLA13 obtained in Preparation Example 2, and GSA obtained in Comparative Preparation Example 1 in water are shown in FIG. 2.

As shown in FIG. 2, GSA and GLA were relatively well dispersed in water compared to graphite, indicating the presence of hydrophilic carboxylic groups in both GLA and GSA.

Absorption Spectra of Aqueous Solutions of Graphite, GLA, and GSA

Graphite, GLA11, GLA13 and GLA16 obtained in Preparations 1-3, and GSA obtained in Comparative Preparation Example 1 were each dissolved in DE water, and a Perkin-Elmer Lambda 800/900 spectrometer was used to measure the absorption spectra thereof. The results are shown in FIG. 3.

Figure 3:
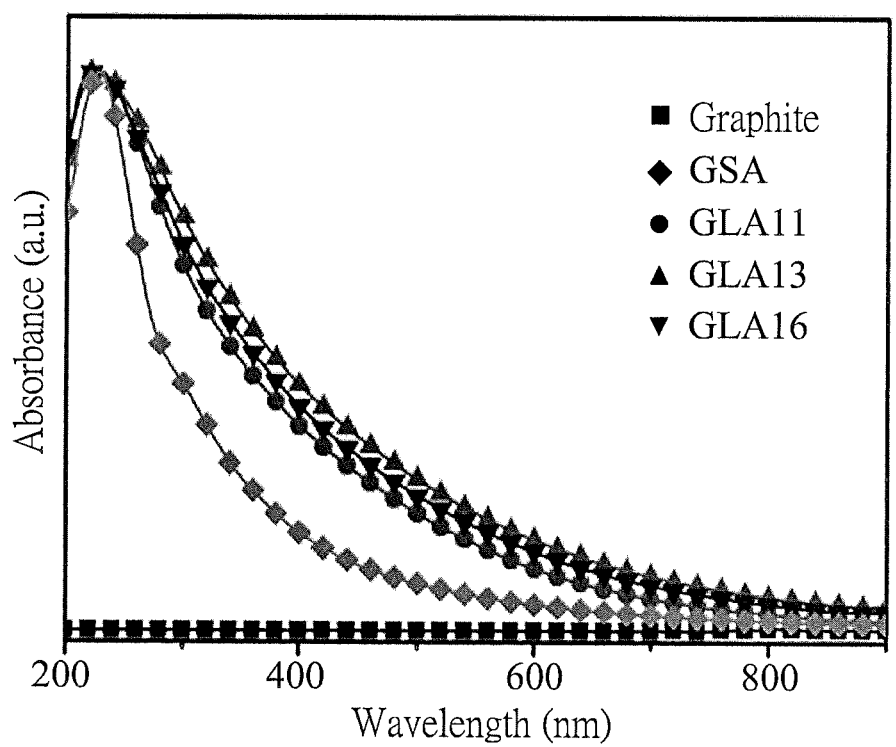
FIG. 3 is a plot illustrating absorption spectra of graphite, modified graphene products (GLA11, GLA13, and GLA16) of Preparation Examples 1-3, and a modified graphene product (GSA) of Comparative Preparation Example 1.

As shown in FIG. 3, all of GLA11, GLA13 and GLA16 exhibited an absorption peak at 226 nm, which corresponds to the $\pi$-$\pi^*$ transition of an aromatic C=C absorption band and the n-$\pi^*$ transition of a C=O absorption band, which indicates that GLA11, GLA13 and GLA16 obtained in Preparation Examples 1-3 are reduced graphene oxide having a linking moiety of —(C=O)—X—COOH.

Additionally, the absorption intensities of GLA11, GLA13, and GLA16 at wavelengths greater than 300 nm increased more significantly than that of GSA, which indicates that GLA has a greater degree of conjugation than GSA. In the Hummers' method used in Comparative Preparation Example 1, the addition of a strong oxidizing agent destroys plane and edge structures and forms acid groups and other oxygen-containing groups. However, in the Friedel-Crafts acylation reaction in Preparation Examples 1-3, electrophilc aromatic substitution occurred on the structure with the highest electron density (edge site).

Notably, as shown in FIG. 3, compared to GLA11 and GLA 16, GLA13 has a higher absorption intensity in a wavelength range from 200 to 900 nm, which indicates that the amount of the linking moiety of —(C=O)—X—COOH contained in GLA13 is greater than those contained in GLA11 and GLA16.

X-ray Photoelectron Spectroscopy Analysis of Graphite and GLA:

The C1s spectra of graphite and GLA 13 obtained in Preparation Example 2 were examined using an X-ray photoelectron spectrometer (VG Scientific ESCALAB 250 series). The results for graphite and GLA13 are shown in FIG. 4 and FIG. 5, respectively.

Figure 4:
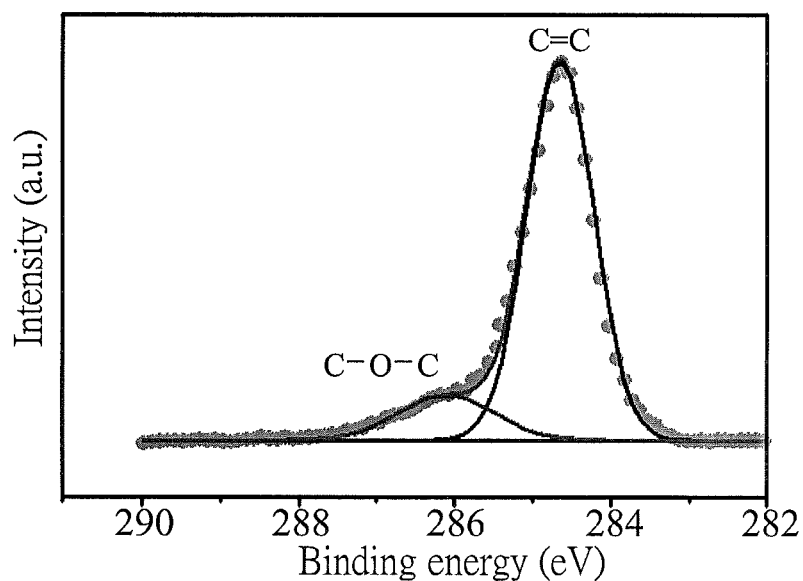
FIG. 4 is a plot illustrating an X-ray photoelectron spectrum of graphite.

As shown in FIG. 4, The C1s spectrum of graphite was deconvoluted into two peaks, which correspond respectively to the aromatic ring (C=C/C—C) at 284.6 eV and the original defective structure of hydroxyl group and epoxy/ether group (C—O—C) at 286.1 eV. The degree of defective structure was determined to be 14.0% by calculating a ratio of an area of defective structure to a total area.

Figure 5:
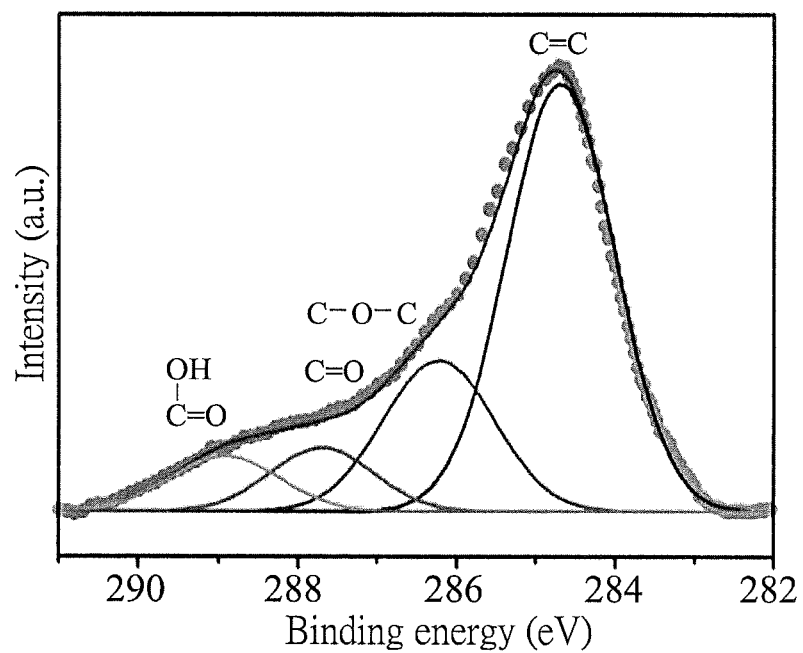
FIG. 5 is a plot illustrating an X-ray photoelectron spectrum of the modified graphene product (GLA13) of Preparation Example 2.

As shown in FIG. 5, GLA13 was deconvoluted into four peaks, in which the peak at 287.7 eV (C=O of ketone) and the peak at 288.9 eV (O—C=O) have area ratios of 8.7% and 8.7%, respectively. The hinging energies of these two peaks are consistent with the theoretical values for 1-one-butenoic acid, which is a chain derived from the ring-opening reaction of maleic acid. Compared to graphite, the degree of defective structure did not significantly increase in GLA13, which indicates that the conjugated structure remained nearly complete in GLA13.

Figure 6:
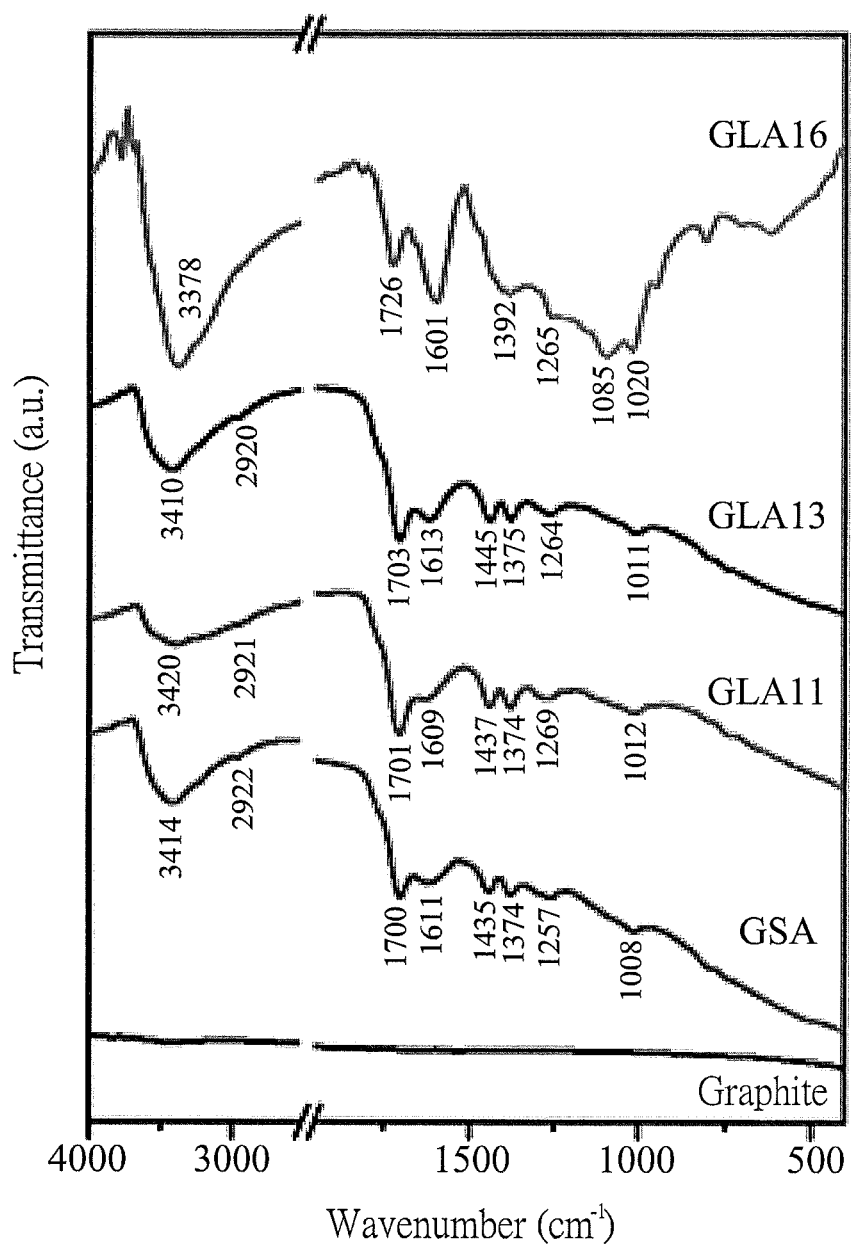
FIG. 6 is a plot illustrating Fourier transform infrared (FT-IR) spectra of graphite, the modified graphene products (GLA11, GLA13, and GLA16) of Preparation Examples 1-3, and the modified graphene product (GSA) of Comparative Preparation Example 1.

Fourier-transform Infrared (FT-IR) Spectroscopy Analysis of Graphite, GLA, and GSA:

FT-IR spectra of graphite, GLA11, GLA13 and GLA16 obtained in Preparation Examples 1-3, and GSA obtained in Comparative Preparation Example 1 were examined respectively using a Bruker-Tensor 27 FT-IR spectrometer (spectral resolution: 8 cm$^{-1}$). The results are shown in FIG. 6.

A typical band characteristic of graphite at 1530 cm$^{-1}$ was assigned to stretch vibration of C=C ($v_{C=C}$). As can be observed from the spectrum of GLA13 shown in FIG. 6, after Friedel-Crafts acylation, GLA13 exhibited several new peaks at 1703 cm$^{-1}$ ($v_{C=O}$), 1613 cm$^{-1}$ ($v_{C=C}$ of graphene overlapping $v_{C=C}$ of ketone), 1445 cm$^{-1}$ and 1264 cm$^{-1}$ (coupling between the in-plane O—H bending and the C—O stretching of the dimer), and 1375 cm$^{-1}$ (—CH$_2$ bending). Peaks characteristic of the asymmetric and symmetric $v_{C=O}$ of maleic acid were not observed at 1869 or 1777 cm$^{-1}$, which confirms the formation of 1-one-butenoic acid (i.e., —(C=O)—CH=CH—COOH) at the edge site after the ring-opening reaction of maleic acid. The presence of 1-one-butenoic acid facilitates dispersion of GLA in water due to negative charge repulsion of anion generated by dissociation.

Carboxylic Group Density Analysis of Graphite, GLA, and GSA:

Toluidine blue O (TBO) was used as a probe (*Surf Coat. Technol.*, vol. 205, S534-S536) to quantify carboxylic group densities (quantities of carboxylic group (mol) per mg of graphite, GLA, or GSA) of graphite, GLA11, GLA13 and GLA16 of Preparation Examples 1-3, and GSA of Comparative Preparation Example 1 based on the absorption spectra at 633 nm. The results are shown in FIG. 7 (n=3).

Figure 7:
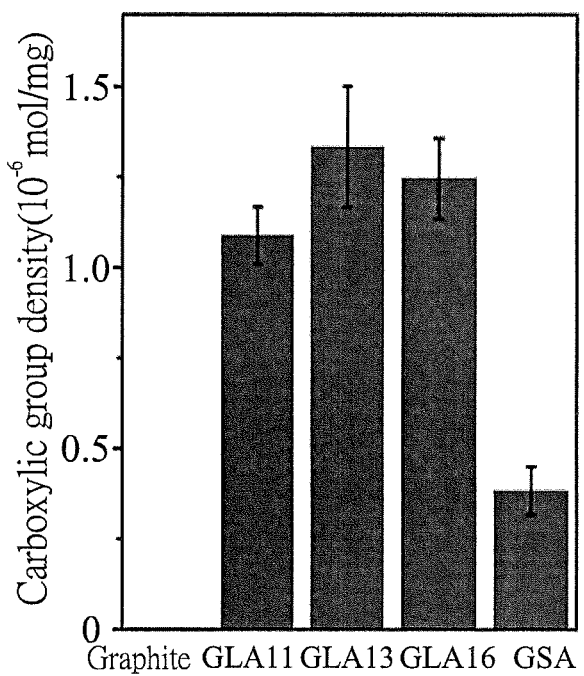
FIG. 7 is a bar chart illustrating a comparison of the hydroxyl group densities of graphite, the modified graphene products (GLA11, GLA13, and GLA16) of Preparation Examples 1-3, and the modified graphene product (GSA) of Comparative Preparation Example 1.

As shown in FIG. 7, the carboxylic group densities of GLA11, GLA13, and GLA16 are significantly higher than that of GSA (0.38×10$^{-6}$ mol/mg), which indicates that GLA11, GLA13, and GLA16 have more carboxylic groups (—(C=O)—CH=CH—COOH) as linking moiety for bonding antibodies. Specifically, GLA13 exhibited a much higher carboxylic group density (1.33×10$^{-6}$ mol/mg).

Thermal Gravimetric Analysis of Graphite, GLA, and GSA:

A thermal gravimetric analysis of graphite, GLA13 obtained in Preparation Example 2, and GSA obtained in Comparative Preparation Example 1 was performed from 100° C. to 690° C. The results are shown in FIG. 8.

Figure 8:
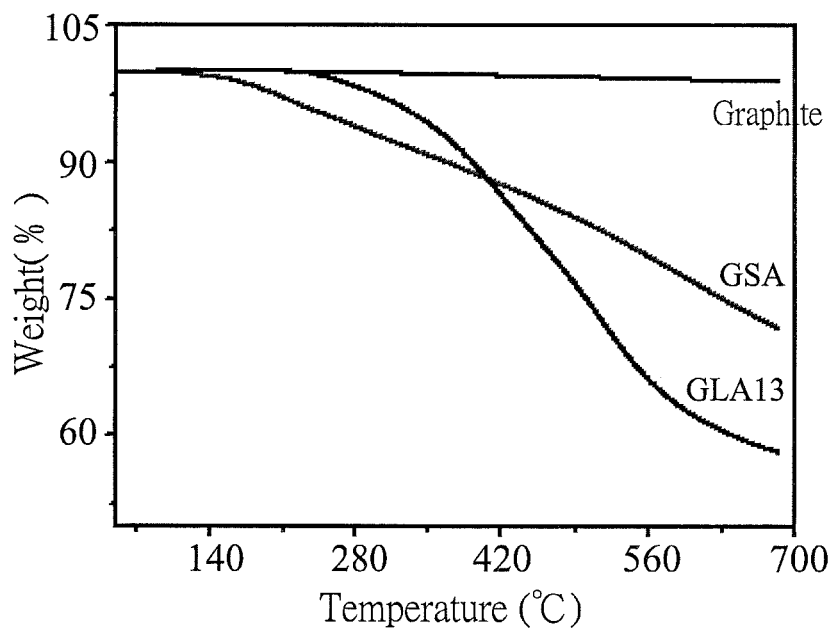
FIG. 8 is a plot illustrating thermogravimetric analysis spectra of graphite, the modified graphene product (GLA13) of Preparation Example 2, and the modified graphene product (GSA) of Comparative Preparation Example 1.

As shown in FIG. 8, due to the high structural strength of graphite, little weight loss was observed for graphite. However, both GLA13 and GSA exhibited significant weight loss due to the destruction of the structure during chemical modification and the instability of the side chain. GSA initially exhibited weight loss at approximately 100° C. Compared to GSA, GLA13 exhibited higher thermal stability, with initial weight loss occurring at 240° C., which indicates that enhanced preservation of the graphene structure improved side chain stability. Additionally, the total weight loss of GLA13 was greater than that of GSA, which indicates that GLA13 has side chains with a higher molecular weight and a higher degree of grafting of 1-one-butenoic acid group (—(C=O)—CH=CH—COOH).

X-ray Diffraction Analysis of Graphite and GLA:

Each of graphite and GLA11, GLA13, and GLA16 of Preparation Examples 1-3 was mixed with nickel powder (15% w/w), and was then analyzed using a X-ray diffractometer (Rigaku D/Max-2B) together with a nickel-filtered Cu Kα radiation analysis (scan rate: 1°/min, scanning range: 5°-90°). The results are shown in FIG. 9.

Figure 9:
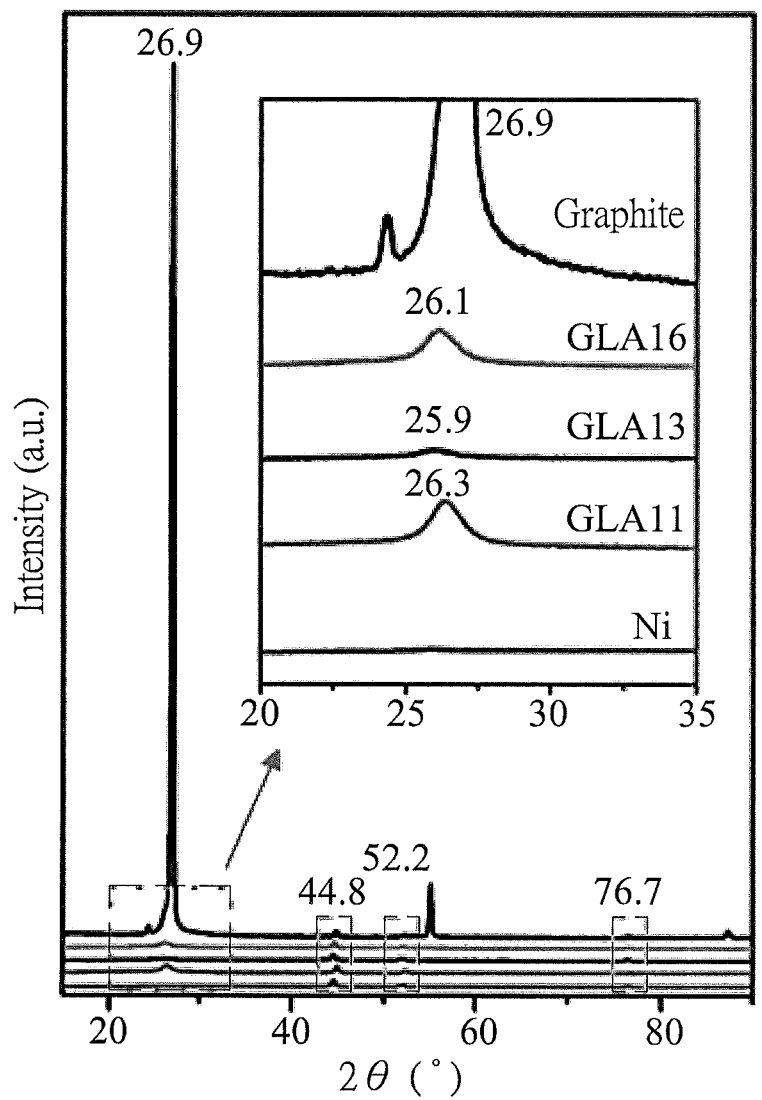
FIG. 9 is a plot illustrating X-ray diffraction (XRD) spectra of Ni, graphite, and the modified graphene products (GLA11, GLA13, and GLA 16) of Preparation Examples 1-3.

As shown in FIG. 9, GLA11, GLA13, and GLA16 yielded diffraction peaks at 44.8°, 52.2°, and 76.7°. In addition, graphite exhibited two diffraction peaks at 26.9° and 55.0° due to crystalline heavy stacking. As can be observed from the spectra of GLA11, GLA13, and GLA16, the diffraction peak 26.9° for graphite decreased in size and shifted to a lower angle, while the diffraction peak at 55.0° for graphite disappeared. These results indicate that the heavy stacking was destroyed due to exfoliation of graphite into graphene.

Transmission Electron Microscopy (TEM) Analysis of GLA and MGLA:

TEM analysis of GLA11, GLA13, GLA16 obtained in Preparation Examples 1-3 and MGLA obtained in Preparation Example 4 was performed using a transmission electron microscope (Hitachi H-7500 series). TEM images for GLA11, GLA13, GLA16, and MGLA are shown in FIGS. 10-13, respectively.

Figure 10:
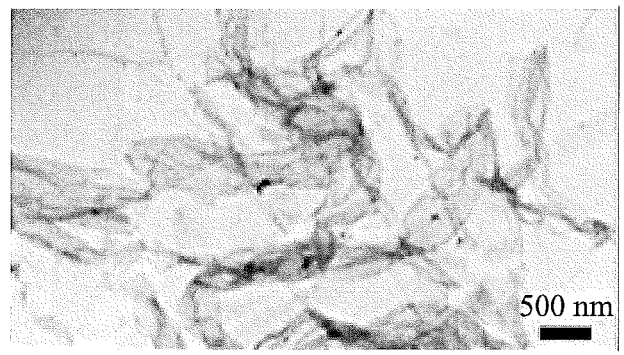
FIG. 10 is a transmission electron microscopic (TEM) image illustrating a structure of the modified graphene product (GLA11) of Preparation Example 1.
Figure 11:
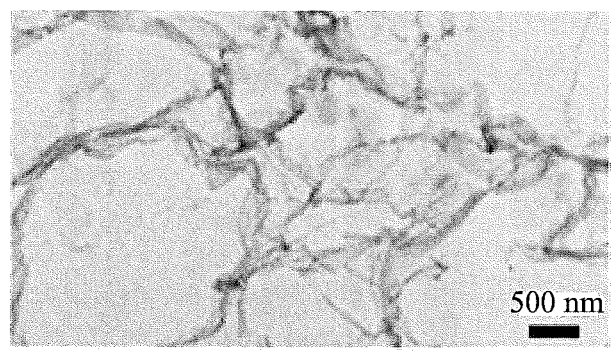
FIG. 11 is a TEM image illustrating a structure of the modified graphene product (GLA13) of Preparation Example 2.
Figure 12:
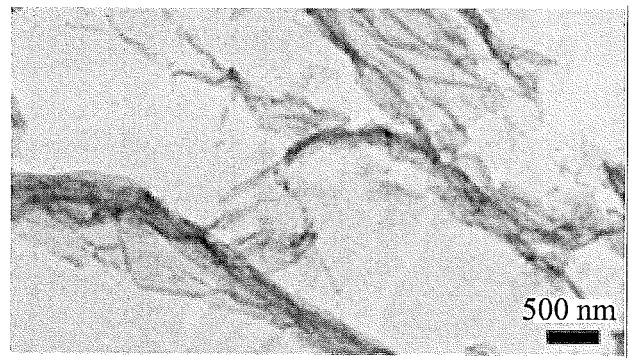
FIG. 12 is a TEM image illustrating a structure of the modified graphene product (GLA16) of Preparation Example 3.

As shown in FIGS. 10-12, each of GLA11, GLA13, GLA16 has a transparent thin sheet with a wrinkled appearance, which is in agreement with the structural feature of a graphene sheet. This result demonstrates that graphite can be functionalized and exfoliated into graphene via Friedel-Crafts acylation.

Figure 13:
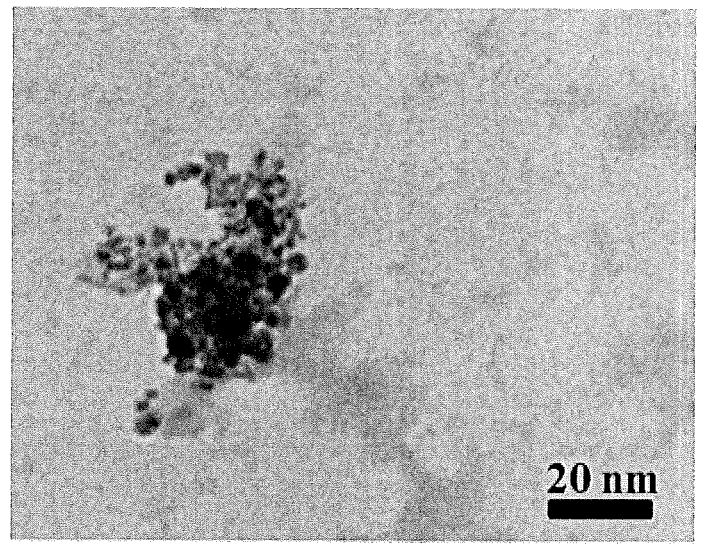
FIG. 13 is a TEM image illustrating a structure of the magnetized modified graphene product (MGLA) of Preparation Example 4.

As shown in FIG. 13, MGLA was miniaturized to a composite of a size of approximately 40 nm and was covered with Fe$_3$O$_4$ magnetic nanoparticles (average particle diameter: 5 nm). Moreover, no free nanoparticles were observed either within or dispersed around the composite. These results indicate that the nanoparticles were adsorbed on GLA, while free nanoparticles were displaced during purification.

Absorption Spectrum Analysis of Aqueous Solutions of Fe$_3$O$_4$, GLA, and MGLA:

Fe$_3$O$_4$ magnetic nanoparticles, GLA13 obtained in Preparation Example 2, and MGLA obtained in Preparation Example 4 were each dissolved in DE water, and the absorption spectra thereof were examined using a Perkin-Elmer Lambda 800/900 absorption spectrometer. The results are shown in FIG. 14.

Figure 14:
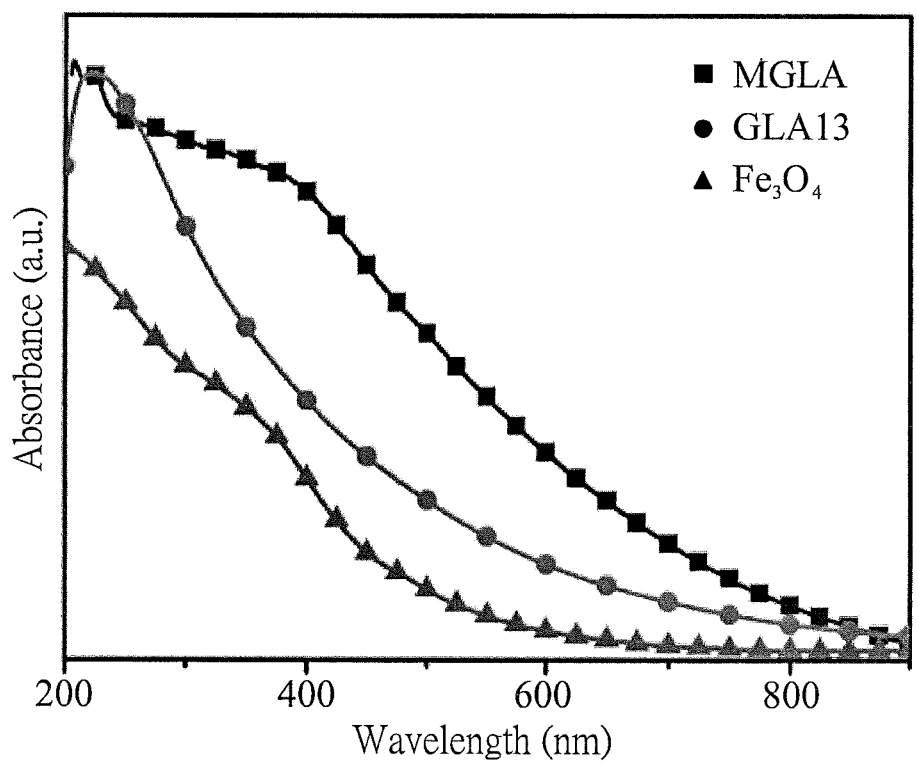
FIG. 14 is a plot illustrating absorption spectra of iron oxide ($Fe_3O_4$), the modified graphene product (GLA13) of Preparation Example 2, and the magnetizied modified graphene product (MGLA) of Preparation Example 4.

As shown in FIG. 14, compared with the absorption band of GLA, a new shoulder corresponding to the Fe$_3$O$_4$ magnetic nanoparticles was observed at approximately 400 nm in MGLA. This result demonstrates that the nanoparticles on the surface of GLA are Fe$_3$O$_4$, confirming the synthesis of MGLA.

Magnetic Analysis of GLA and MGLA:

GLA13 obtained in Preparation Example 2 and MGLA obtained in Preparation Example 4 were each dissolved in water, and the magnetic properties thereof were examined using a magnet. The results are shown in FIG. 15.

Figure 15:
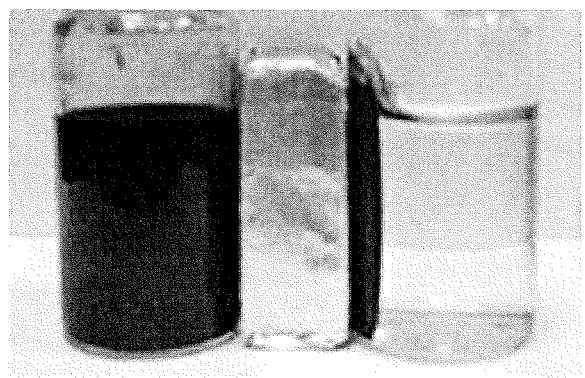
FIG. 15 is a photo illustrating magnetic analysis results for the modified graphene product (GLA13) of Preparation Example 2 and the magnetized modified graphene product (MGLA) of Preparation Example 4.

As shown in FIG. 15, MGLA was drawn to one side of the bottle due to the attraction of the magnet, while GLA was still dispersed in water. The result confirms that MGLA was synthesized.

X-ray Diffraction (XRD) Analysis of GLA and MGLA:

GLA13 obtained in Preparation Example 2 and MGLA obtained in Preparation Example 4 were each examined using an X-ray diffractometer (Rigaku D/Max-2B). The results are shown in FIG. 16.

Figure 16:
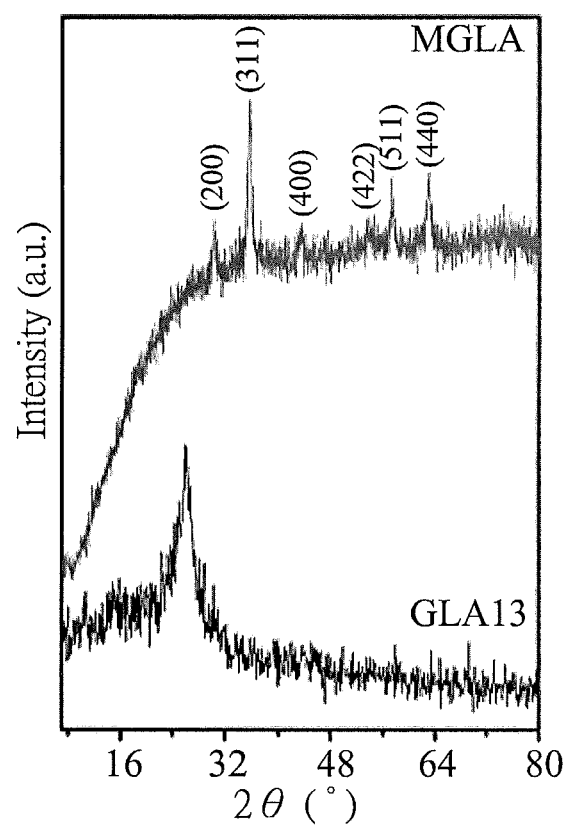
FIG. 16 is a plot illustrating XRD spectra of the modified graphene product (GLA13) of Preparation Example 2 and the magnetized modified graphene product (MGLA) of Preparation Example 4.

As shown in FIG. 16, as compared to GLA, six new diffraction peaks at 30.4°, 35.8°, 43.5°, 53.7°, 57.3°, and 63.1° were attributed to the crystalline Fe$_3$O$_4$. The result further confirms that MGLA was synthesized.

Fourier-transform Infrared (FT-IR) Spectroscopy Analysis of Fe$_3$O$_4$, GLA, and MGLA:

FT-IR spectra of Fe$_3$O$_4$, GLA13 obtained in Preparation Example 2, and MGLA obtained in Preparation Example 4 were each examined using a Bruker-Tensor 27 FT-IR spectrometer (spectral resolution: 8 cm$^{-1}$). The results are shown in FIG. 17.

Figure 17:
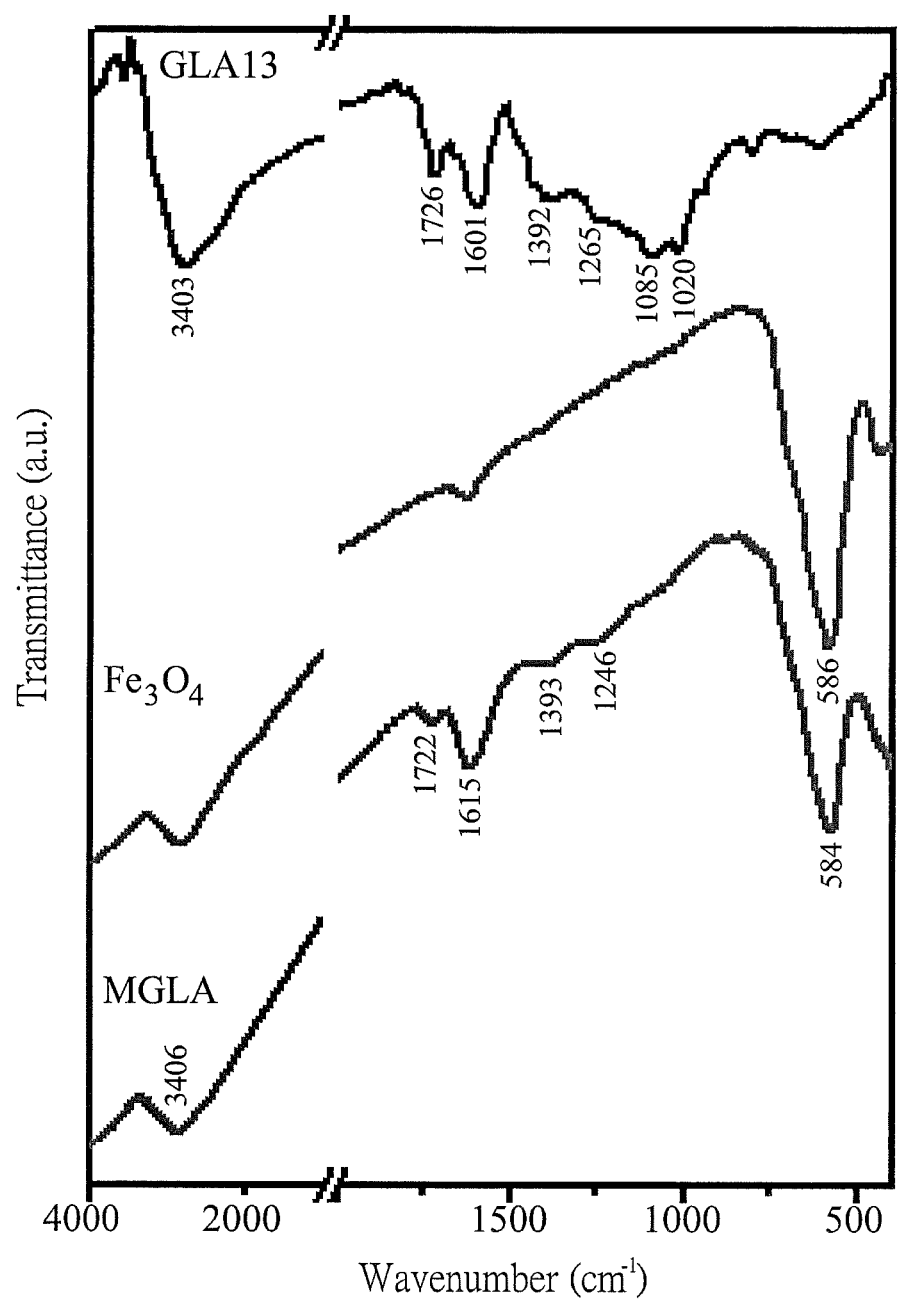
FIG. 17 is a plot illustrating FT-IR spectra of iron oxide ($Fe_3O_4$), the modified graphene product (GLA13) of Preparation Example 2, and the magnetized modified graphene product (MGLA) of Preparation Example 4.

As shown in FIG. 17, FT-IR spectroscopy revealed a characteristic peak of Fe—O at 584 cm$^{-1}$ in MGLA, which is a slight red shift on the order of 2 cm$^{-1}$ compared to Fe$_3$O$_4$ nanoparticles. This result reveals that interaction between GLA and Fe$_3$O$_4$ increase adsorption.

Magnetization Synthesis of GLA, MGLA, and MGSA:

Magnetization synthesis of each of GLA13 obtained in Preparation Example 2, MGLA obtained in Preparation Example 4, and MGSA obtained in Comparative Preparation Example 2 was performed using a superconducting quantum interference device (SQUID, Quantum Design MPMS7). The results are shown in FIG. 18.

Figure 18:
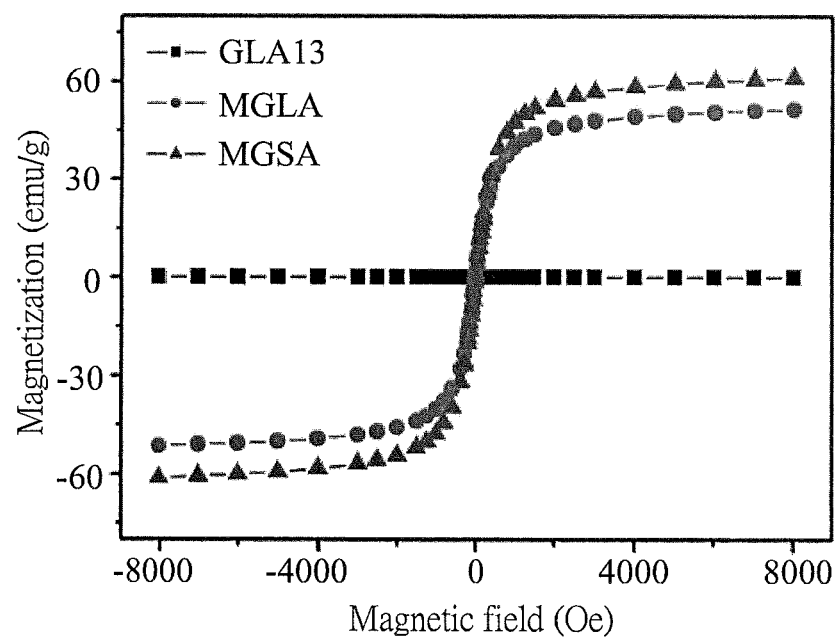
FIG. 18 is a plot illustrating magnetization curves of the modified graphene product (GLA13) of Preparation Example 2, the magnetized modified graphene product (MGLA) of Preparation Example 4, and a magnetized modified graphene product (MGSA) of Comparative Preparation Example 2.

As shown in FIG. 18, magnetizations of GLA and MGLA are respectively 0 emu/g and 51.0 emu/g. In addition, the magnetization of MGSA is 61.0 emu/g, which is higher than that of MGLA (51.0 emu/g). The increased magnetization of MGSA is most likely due to the destruction of the GSA structure and associated oxygen groups, which favors adsorption of Fe$_3$O$_4$ nanoparticles.

Carboxylic Group Density Analysis of MGLA and MGSA:

Toluidine blue O (TBO) was used as a probe (*Surf. Coat. Technol.*, vol. 205, S534-S536) to quantify carboxylic group densities (quantity of carboxylic groups (mol) per mg of MGLA or MGSA) of MGLA obtained in Preparation Example 4 and MGSA obtained in Comparative Preparation Example 2 based on the absorption spectrum at 633 nm. The results are shown in FIG. 19.

Figure 19:
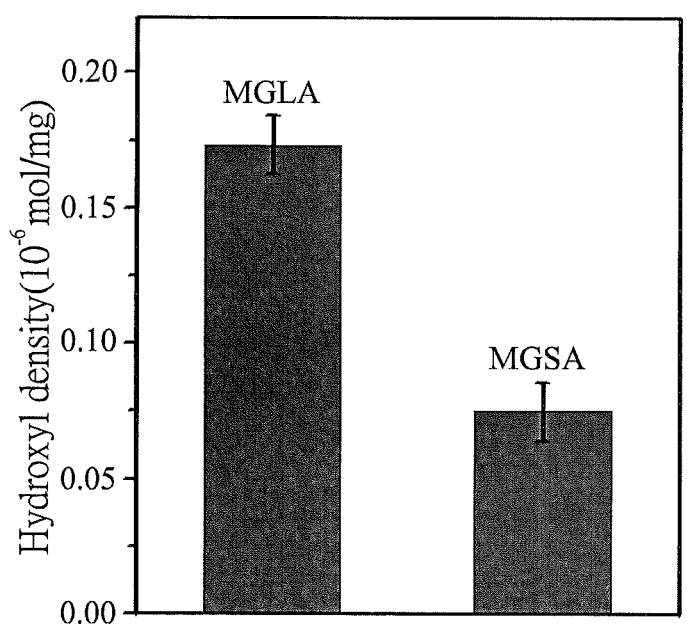
FIG. 19 is a bar chart illustrating a comparison of the hydroxyl group densities of the magnetized modified graphene product (MGLA) of Preparation Example 4 and the magnetizied modified graphene product (MGSA) of Comparative Preparation Example 2.

As shown in FIG. 19, the carboxylic group densities of MGLA and MGSA after magnetization decreased significantly to $0.17 \times 10^{-6}$ mol/mg and $0.08 \times 10^{-6}$ mol/mg, respectively, which are lower than that of GLA ($1.33 \times 10^{-6}$ mol/mg) and that of GSA ($0.38 \times 10^{-6}$ mol/mg), respectively. This finding suggests that the highly alkaline solution used during the magnetizing process cleaved the acid chain (i.e., carboxylic group).

Quantification of Urinary Apolipoprotein A II (APOA2) and Clinical Importance for Bladder Cancer:

(a) Collection of Clinical Urinary Specimen:

Clinical specimens were collected using a method described in *J. Proteome Res.*, vol. 9, p 5803-5815 and *J. Proteomics*, vol. 75, p 3529-3545. The method essentially includes the following steps:

Step 1: first-morning urine samples were collected from hernia patients (controls) and bladder cancer patients into containers that contained a protease inhibitor cocktail tablet (one tablet per 50 ml of urine; Roche, Mannheim, Germany) and sodium azide (1 mM).

Step 2: The collected urine samples from step 1 were centrifuged at 5000×g for 30 min at 4° C. within 5 hours of collection to remove cells and debris, and the clarified supernatants were stored at −80° C. until further processing.

All clinical samples were collected from the Department of Urology, Chang Gung Memorial Hospital, Taoyuan, Taiwan.

(b) APOA2 Protein Quantification in Individual Urine Samples using Bio-Plex Assay:

The level of APOA2 apolipoprotein in each of the urine samples was determined with a MILLIPLEX MAP Human Apolipoprotein Panel kit (Millipore, Mass., USA) using a Bio-Plex system (Bio-Rad Laboratories). The assay procedure was a modification of a blood sample-suitable protocol provided by Millipore. Immunobeads were analyzed using Bio-Plex 200 system (Bio-Rad Laboratories). Standard curves and analyte concentrations were obtained using a Bio-Plex Manager software version 4.2 (Bio-Rad Laboratories).

In total, 20 urine samples, in which 10 urine samples were from hernia patients and 10 urine samples were from patients with bladder cancer, were analyzed using a Human Apolipoprotein Kit, which is commercially available as a 96-well plate immunoassay. The results are shown in FIG. 20.

Figure 20:
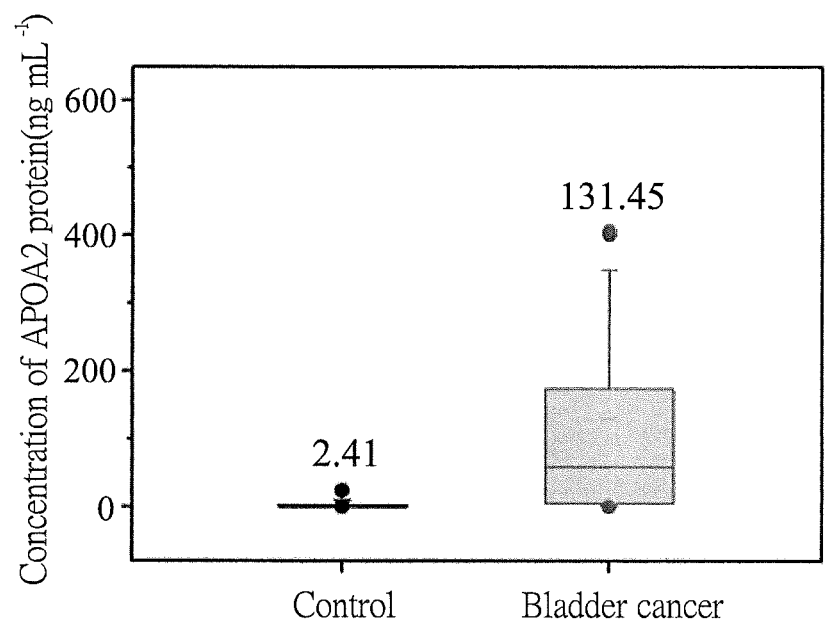
FIG. 20 is a plot illustrating analysis results for urinary samples of hernia patients (controls) and bladder cancer patients using a Bio-Plex assay.

(c) Results and Discussion:

As shown in FIG. 20, an average level of APOA2 apolipoprotein in the urine samples of bladder cancer patients is 131.45 ng/mL, which is approximately 54.5-fold higher than that (2.41 ng/mL) in the urine samples of hernia patients (n=48 for hernia patient controls, and n=63 for bladder cancer patients; p<0.001; area under the curve (AUC) =0.864). The higher urinary concentration of APOA2 in bladder cancer patients was confirmed by an immune-based Bio-Plex system, indicating that bladder cancer may be diagnosed by the level of APOA2 apolipoprotein in a urine sample of a patient with bladder cancer.

Figure 21:
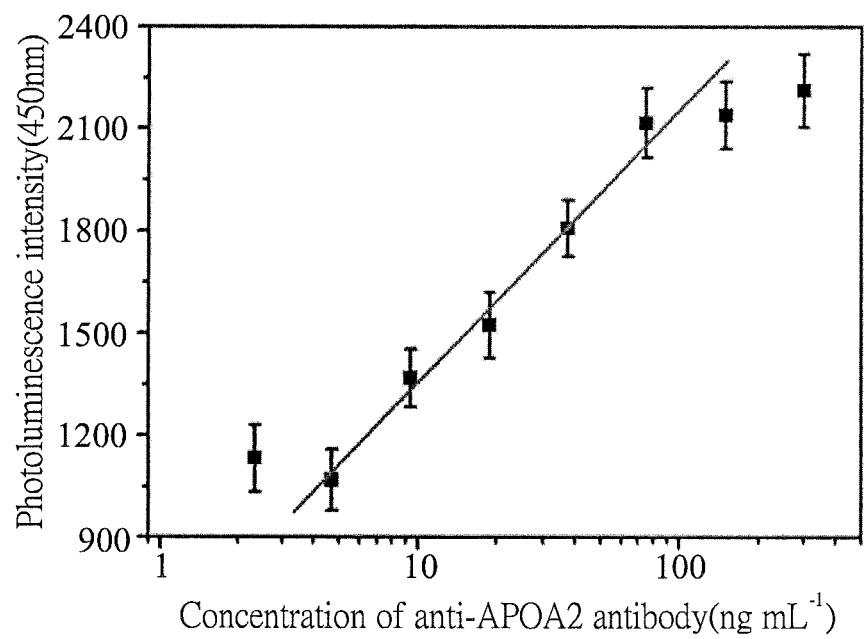
FIG. 21 is a plot illustrating an optical density calibration curve of an anti-APOA2 antibody.

Quantification of Anti-APOA2 Antibody using an Enzyme-Linked Immunosorbent Assay (ELISA):

300, 150, 75, 37.5, 18.8, 9.4, 4.7 and 2.3 ng/mL of solutions of anti-APOA2 antibody in PBS (150 μl for each solution) were coated on a Microlite 2 multiwell plate of an ELISA reader (Thermo Labsystems, Franklin, Mass.) for 1.5 hours. After washing with PBS, 150 μl of a solution of BSA in PBS (5 mg/ml) was used as block for 1.5 hours before hybridization with 1.95 μg/ml of a solution of APOA2 protein in PBS (150 μl) for 1.5 hours. A total of 150 μl of a solution of BSA in PBS (5 mg/ml) was used for further blocking. 100 μl of biotin-antibody was added to each well and incubated for 1 hour at 37° C. After removing the solution, 90 μl of TMB substrate was added to each well and incubated for 30 minutes. Finally, 50 μl of a stop solution was added to each well and the plate was gently tapped to ensure thorough mixing. The photoluminescence intensity at 450 nm of each well was measured within 5 minutes. An optical density calibration curve of anti-APOA2 antibody is shown in FIG. 21 (n=3). All processes were performed at 37° C. in a dark room.

Figure 22:
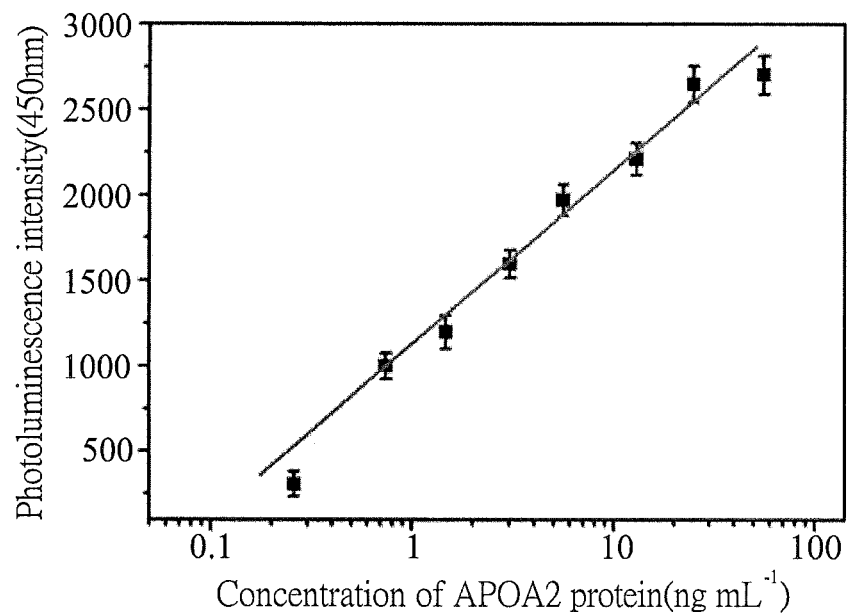
FIG. 22 is a plot illustrating an optical density calibration curve of an APOA2 protein.

Quantification of APOA2 Protein using ELISA Assay:

10 μg/ml of a solution of anti-APOA2 antibody in PBS (150 μl) was coated on a Microlite 2 multiwell plate of an ELISA reader (Thermo Labsystems, Franklin, Mass.) for 1.5 hours. After washing with PBS, 150 μl of a solution of BSA in PBS (5 mg/ml) was used as block for 1.5 hours before hybridization with 55.7, 24.8, 12.9, 6.5, 3.2, 1.6, 0.8 and 0.4 ng/ml of solutions of APOA2 protein in PBS (150 μl for each solution) for 1.5 m hours. A total of 150 μl of a solution of BSA in PBS (5 mg/ml) was used for furthering blocking. 100 μl of a solution of biotin-antibody in PBS was added to each well and incubated for 1 hour at 37° C. After removing the solution, 90 μl of TMB substrate was added to each well and incubated for 30 minutes. Finally, 50 μl of a stop solution was added to each well and the plate was gently tapped to ensure thorough mixing. The photoluminescence intensity at 450 nm of each well was measured within 5 minutes. An optical density calibration curve of APOA2 protein is shown in FIG. 22 (n=3). All processes were performed at 37° C. in a dark room.

Loaded Quantity Analysis of Anti-APOA2 Antibody (Ab) of Ab-MGLA and Ab-MGSA:

The loaded quantity (ng) of anti-APOA2 antibody (Ab) in each of Ab-MGLAs obtained in Preparation Examples 5-10 and in each of Ab-MGSAs obtained in Comparative Preparation Examples 3-8 was obtained by measuring the photoluminescence intensity at 450 nm using an ELISA reader (i.e., monitoring the quantity of the un-immobilized Ab) and calculating the loaded quantity (ng) of anti-APOA2 antibody (Ab) based on the optical density calibration curve of anti-APOA2 antibody shown in FIG. 21. The plots of the loaded quantity (ng) of anti-APOA2 antibody (Ab) in Ab-MGLAs and Ab-MGSAs versus the amounts of the anti-APOA2 antibody shown in Tables 2 and 4 for preparing Ab-MGLAs and Ab-MGSAs are shown in FIG. 23 (n=3).

Figure 23:
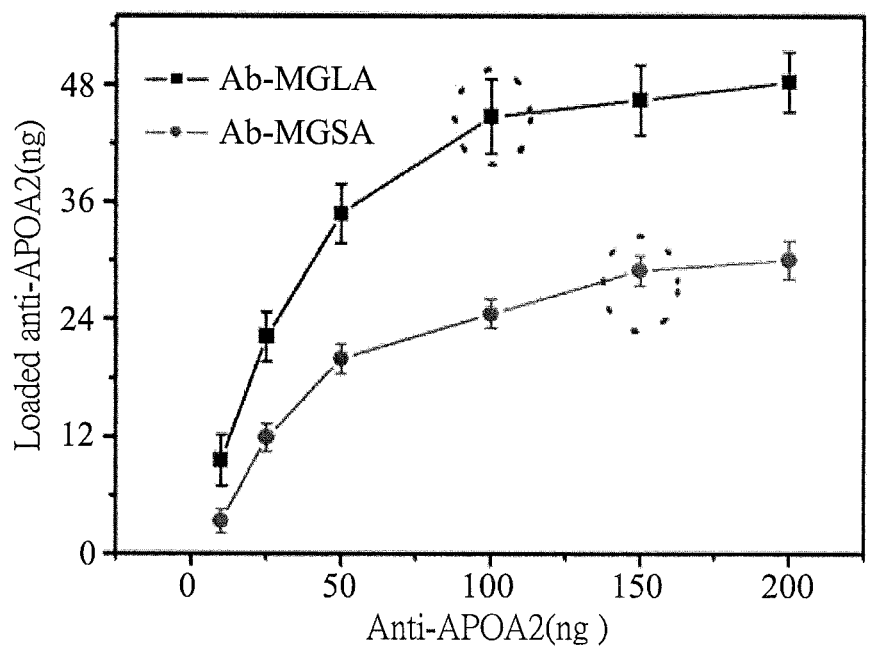
FIG. 23 is a curve plot illustrating the weight relationship between the anti-APOA2 antibody immobilized to Ab-MGLA and the anti-APOA2 added in the preparation of Ab-MGLA and the weight relationship between the anti-APOA2 antibody immobilized to Ab-MGSA and the anti-APOA2 added in the preparation of Ab-MGSA.

As shown in FIG. 23, the optimal amount of Ab immobilized on 1 μg of MGLA was approximately 42 ng (Preparation Example 8), and the optimal amount of Ab immobilized on 2.13 μg of MGSA was approximately 29 ng (Comparative Preparation Example 7).

In addition, the molar amounts of carboxylic groups provided by 1 μg of MGLA and 2.13 μg of MGSA were calculated based on the carboxylic group densities of MGLA and MGSA (i.e., $0.17 \times 10^{-6}$ mol/mg and $0.08 \times 10^{-6}$ mol/mg, respectively) shown in FIG. 19. The loaded quantities in ng of anti-APOA2 antibody (Ab) in Ab-MGLAs and Ab-MGSAs were converted to the loaded quantities in moles (molecular weight of anti-APOA2 antibody (Ab): 17.4 kDa). The antibody bonding ratio may be calculated according to Equation (I) below, and the results are shown in Table 5.

Antibody bonding ratio (%)=(Molar amount of *Ab* bonded to *MGLA* (or *MGSA*)/Molar amount of carboxylic groups provided by *MGLA* (or *MGSA*))×100%   Equation I:

TABLE 5

| | Antibody bonding ratio |
|---|---|
| MGLA (Prep. Ex. 8) | 1.4%(mole/mole) |
| MGSA (Comp. Prep. Ex. 7) | 0.98%(mole/mole) |

As shown in Table 5, the antibody bonding ratio for MGLA is 1.4% (i.e., $2.4 \times 10^{-12}$ mole of anti-APOA2 antibody being bonded by $1.7 \times 10^{-10}$ mole of carboxylic groups). The antibody bonding ratio for MGSA is 0.98% (i.e., $1.67 \times 10^{-12}$ mole of anti-APOA2 antibody being bonded by $1.7 \times 10^{-10}$ mole of carboxylic groups). The molar amount of anti-APOA2 antibody (Ab) bonded by MGLA is 1.43 times of that of anti-APOA2 antibody (Ab) bonded by MGSA.

Compared to MGSA, the linking moiety (i.e., —(C=O)—CH=CH—(C=O)—) contained in MGLA has a greater carbon number (i.e. 4 carbon atoms). Therefore, the linking moiety contained in MGLA has more freedom as compared to MGSA so that steric hindrance during the immobilization of the antibody may be prevented and the amount of the immobilized antibody may be increased.

Bioactivity Analysis of Anti-APOA2 Antibody (Ab) of Ab-MGLA and Ab-MGSA using an Enzyme-Linked Immunosorbent Assay (ELISA):

(a) Analysis Method:

Step 1: Ab-MGLA obtained in Preparation Example 8 and Ab-MGSA obtained in Comparative Preparation Example 7 were each dissolved in PBS to prepare solutions of Ab-MGLA and Ab-MGSA in PBS (0.5 mg/ml).

Step 2: 100 μl of each of the solutions of Ab-MGLA and Ab-MGSA (0.5 mg/ml) obtained in Step 1 was coated on a Microlite 2 multiwell plate of an ELISA reader (Thermo Labsystems, Franklin, Mass.) for 1.5 hours. 150 μl of a solution of BSA in PBS (5 mg/ml) was used as block for 1.5 hours before hybridization with 1.95 μg/ml of a solution of APOA2 protein in PBS (150 μl) for 1.5 hours. A total of 150 μl of a solution of BSA in PBS (5 mg/ml) were utilized for further blocking. 100 μl of biotin-antibody was added to each well and incubated for 1 hour at 37° C. After removing the solution, 90

μl of TMB substrate was added to each well and incubated for 30 minutes. Finally, 50 μl of a stop solution was added to each well and the plate was gently tapped to ensure thorough mixing. The photoluminescence intensity at 450 nm of each well was measured within 5 minutes. All process were performed at 37° C. in a dark room and under an additional magnetic field.

The molar amounts of the APOA2 protein bonded to Ab-MGLA and Ab-MGSA were calculated from the measured photoluminescence intensities based on the optical density calibration curve of APOA2 protein shown in FIG. 22. The antibody bioactivity of each of Ab-MGLA and Ab-MGSA was calculated from the loaded quantity of the Anti-APOA2 antibody (Ab) of Ab-MGLA of Preparation Example 8 and Ab-MGSA of Comparative Preparation Example 7 obtained based on FIG. 23 and according to Equation (II) below. The results are shown in Table 6.

Antibody bioactivity (%)=(Molar amount of *APOA2* protein bonded to *AB-MGLA* (or *Ab-MGSA*)/Molar amount of Anti-*APOA2* antibody (*Ab*) bonded to *MGLA* (or *MGSA*))×100%   Equation (II):

TABLE 6

| | Bioactivity of Ab-APOA2(%) |
|---|---|
| Ab-MGLA (Prep. Ex. 8) | 71 |
| Ab-MGSA (Comp. Prep. Ex. 7) | 62 |

(b) Results and Discussion:

As shown in Table 6, the antibody bioactivity of Ab-MGLA is higher than that of Ab-MGSA. The linking moiety contained in Ab-MGSA has a relatively short chain length (i.e., only having one carbon atom), and thus has relatively more steric hindrance when the anti-APOA2 antibody (Ab) is intended to bond the APOA2 protein (molecular weight: 37 kDa) thereto. In addition, the APOA2 protein is subject to charge repulsion due to the negative charge thereof, thereby increasing the difficulty of targeting the APOA2 protein by the Anti-APOA2 antibody (Ab). Therefore, the antibody bioactivity of Ab-MGSA may be negatively affected. Compared to Ab-MGSA, the linking moiety (i.e., —(C=O)—CH=CH—(C=O)—) contained in Ab-MGLA has a relatively long chain length (i.e., having four carbon atoms). Therefore, the linking moiety contained MGLA may extend and bend at random angles to produce a large space for targeting the APOA2 protein, resulting in higher bioactivity of the anti-APOA2 antibody.

Analysis of Influence of Various Concentrations of Ab-MGLA on a Biosensor (Ab-MGLA/Poly-SiNW-FET):

The response currents of the biosensors obtained in Examples 1-4 in 0.5 mM PBS under a gate voltage ($V_G$) from 0 to 3 V were measured using a bias voltage ($V_B$) of 50-mV and at a scan rate of 0.5 V/s, and were used as baseline currents ($I_0$). The results are shown by curves a, b, c, and d in FIG. 24 (a: Example 1, b: Example 2, c: Example 3, and d: Example 4).

In addition, a solution of the APOA2 protein in PBS (5 μl, 1 ng/ml) was injected into a micro-fluid channel of each of the biosensors obtained in Examples 1-4 and was allowed to react for 10 minutes at 27° C. in the dark. The unreacted APOA2 protein was removed by washing three times using PBS (0.5 mM), and PBS (0.5 mM) was re-injected into the microfluid channel. The after-reaction current of the biosensors in 0.5 mM PBS under a gate voltage ($V_G$) from 0 to 3 V was measured using a bias voltage ($V_B$) of 50-mV and at a scan rate of 0.5 V/s. The results are shown by curves a', b', c' and d' in FIG. 24 (a': Example 1, b': Example 2, c': Example 3, and d': Example 4). Relative current change was calculated at $V_G$ of 3V from the baseline current and the after-reaction current at $V_G$ of 3V according to Equation (III) below. The results are shown in Table 7.

Relative current change (%)=(-(after-reaction current (μA)-baseline current (μA))/baseline current (μA))×100    Equation (III):

TABLE 7

| Exs. | Relative Current change (%) |
|---|---|
| 1 | 6.3 |
| 2 | 11.3 |
| 3 | 22.6 |
| 4 | 23.6 |

Figure 24:
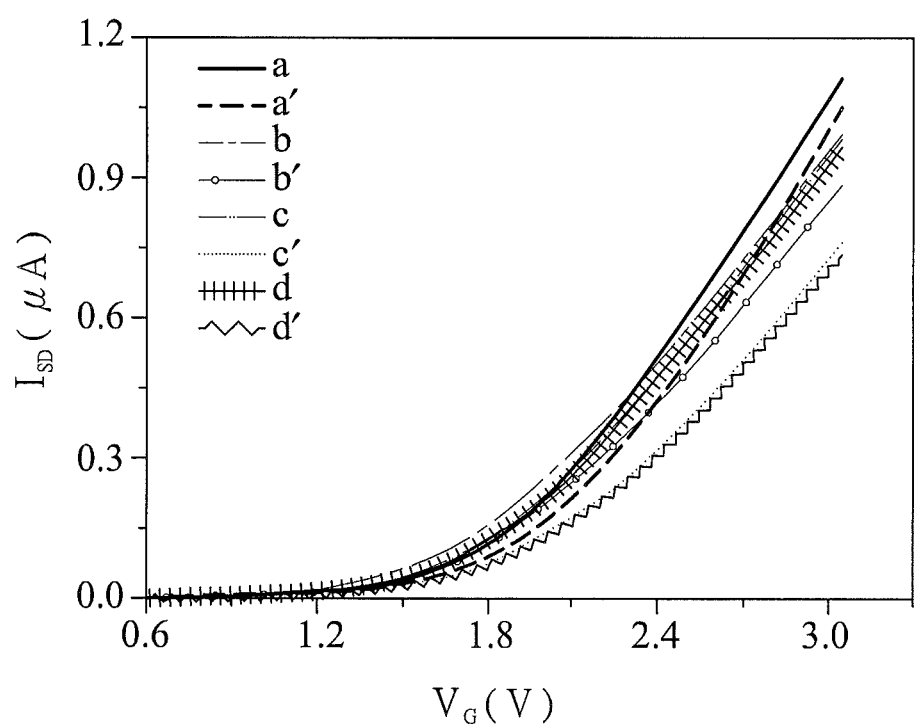
FIG. 24 is an $I_{SD}$-$V_G$ curve plot illustrating current changes of biosensors (Ab-MGLA/poly-SiNW-FET) of Examples 1-4 before and after the addition of the APOA2 protein.

As shown in Table 7, there is no significant difference in the relative current changes between Examples 3 and 4, which indicates that the amount of antibody contained in the biosensor obtained in Example 3 is similar to that in Example 4. In addition, as shown in FIG. 24, the after-reaction current is lower than the baseline current for all of the biosensors obtained in Examples 1-4, which indicates that the charge of the APOA2 protein is negative. After bonding to the biosensors, the APOA2 protein attracted carriers from the substrate to the channel and decreased the conductance between the source and drain electrodes, resulting in decreased current (i.e. conductance).

Analysis of Influence of Interfering Species on a Biosensor (Ab-MGLA/Poly-SiNW-FET):

Immunoglobutin G (IgG), immunoglobutin M (IgM), glucose, ascorbic acid (AA), and uric acid (UA) mentioned hereinafter are species commonly present in human plasma. The original concentrations of these species are typical concentrations in human plasma.

(a) Influence of Interfering Species on a Biosensor (Ab-MGLA/Poly-SiNW-FET) before Addition of APOA2 Protein:

The baseline current ($I_0$) of the biosensor obtained in Example 3 was measured according to the aforesaid procedure. A solution of IgG in PBS at a normal concentration of 1000 ng/dL, a solution of IgM in PBS at a normal concentration of 192.5 mg/dL, a solution of glucose in PBS at a normal concentration of 5 mM, a solution of ascorbic acid in PBS at a normal concentration of 4.3 μg/ml, and a solution of uric acid in PBS at a normal concentration of 0.295 mM were respectively injected into a micro-fluid channel of the biosensor, and the after-reaction current corresponding to each of the solution was measured. After washing using PBS, PBS (0.5 mM) was re-injected into the microfluid channel. The after-reaction current of the biosensor was measured again.

In addition, the solutions of IgG, IgM, glucose, ascorbic acid, and uric acid in PBS at concentrations twice the normal concentrations were each injected into a micro-fluid channel of the biosensor and the after-reaction current of each of the solutions before and after washing was measured according to the aforesaid procedure. $\Delta I/I_0$ (%) was calculated according to equation (IV) below. The results are shown in FIG. 25 (n=3).

Figure 25:
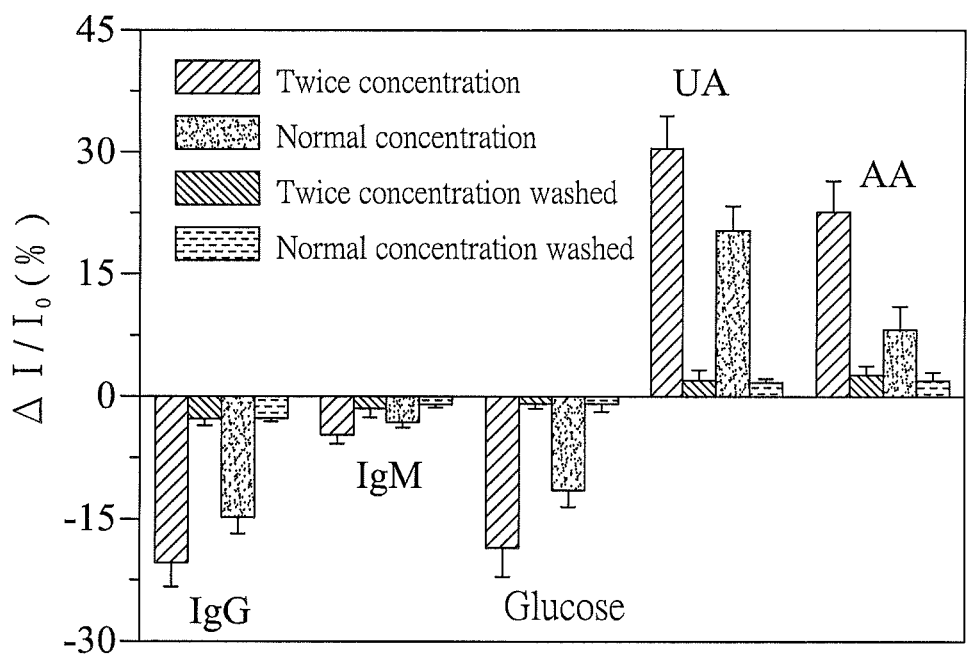
FIG. 25 is a bar chart illustrating the effects of interfering species on current changes of the biosensor (Ab-MGLA/poly-SiNW-FET) of Example 3 before the addition of the APOA2 protein.

$\Delta I/I_0$ (%)=((after-reaction current (μA)-baseline current (μA))/baseline current (μA))×100    Equation IV:

As shown in FIG. 25, the interfering species at a normal concentration and at a concentration twice the normal concentration may vary the current of the biosensor. The current change of the biosensor may be reduced after washing with PBS and re-injecting PBS, which indicates that the interfering species which may affect the measurement result may be removed by washing.

(b) Analysis of Influence of Interfering Species on a Biosensor in the Presence of APOA2 Protein:

The solutions of IgG, IgM, glucose, ascorbic acid, and uric acid in PBS at normal concentrations and at concentrations twice the normal concentrations were each mixed with the APOA2 protein (1 ng) and injected into the microfluid channel of the biosensor. The current corresponding to each of the solutions was measured according to the aforesaid procedure. In addition, a solution of the APOA2 protein in PBS (1 ng/ml) was injected into the micro-fluid channel of the biosensor, and current corresponding to the solution was measured according to the aforesaid procedure. $\Delta I/I_0$ (%) was calculated according to the aforesaid equation (IV). The results are shown in FIG. 26.

Figure 26:
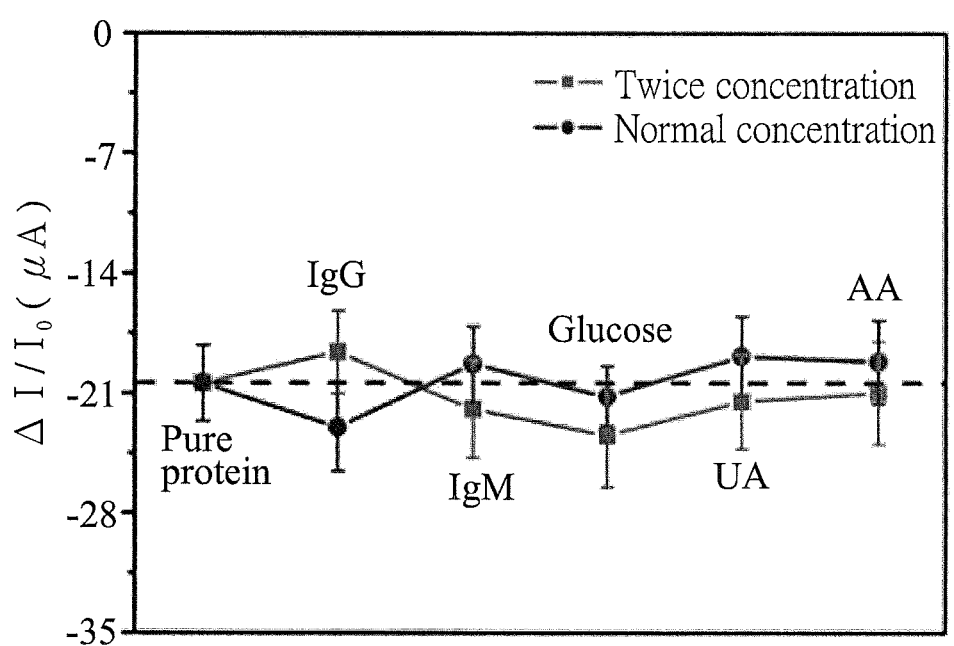
FIG. 26 is a plot illustrating the effects of interfering species on current changes of the biosensor (Ab-MGLA/poly-SiNW-FET) of Example 3 in the presence of the APOA2 protein.

As shown in FIG. 26, there are differences in the results between the situation in which the APOA2 protein is present without the interfering species and the situation in which the APOA2 protein is present together with the interfering species, which indicates that interactions between the protein and interfering species affect binding of the APOA2 protein to the antibody contained in the biosensor.

Analysis of Influence of Concentration of APOA2 Protein on a Biosensor:

(a) Influence of Concentration of APOA2 Protein on a Biosensor of Ab-MGLA/Poly-SiNW-FET:

The baseline current ($I_0$) of the biosensor obtained in Example 3 was measured in 0.5 mM PBS (concentration of APOA2 protein: 0) according to the aforesaid procedure. In addition, solutions of the APOA2 protein in PBS (5 μl for each solution, concentrations ranging from 19.5 pg/ml to 1.95 μg/ml) were each injected into a micro-fluid channel of the biosensor obtained in Example 3 and were allowed to react for 10 minutes at 27° C. in the dark. The unreacted APOA2 protein was removed by washing three times using PBS (0.5 mM), and PBS (0.5 mM) was re-injected into the microfluid channel. The after-reaction current of the biosensor in 0.5 mM PBS under a gate voltage ($V_G$) from 0 to 3 V were measured using a bias voltage ($V_B$) of 50-mV at a scan rate of 0.5 V/s. The results were shown in FIG. 27.

Figure 27:
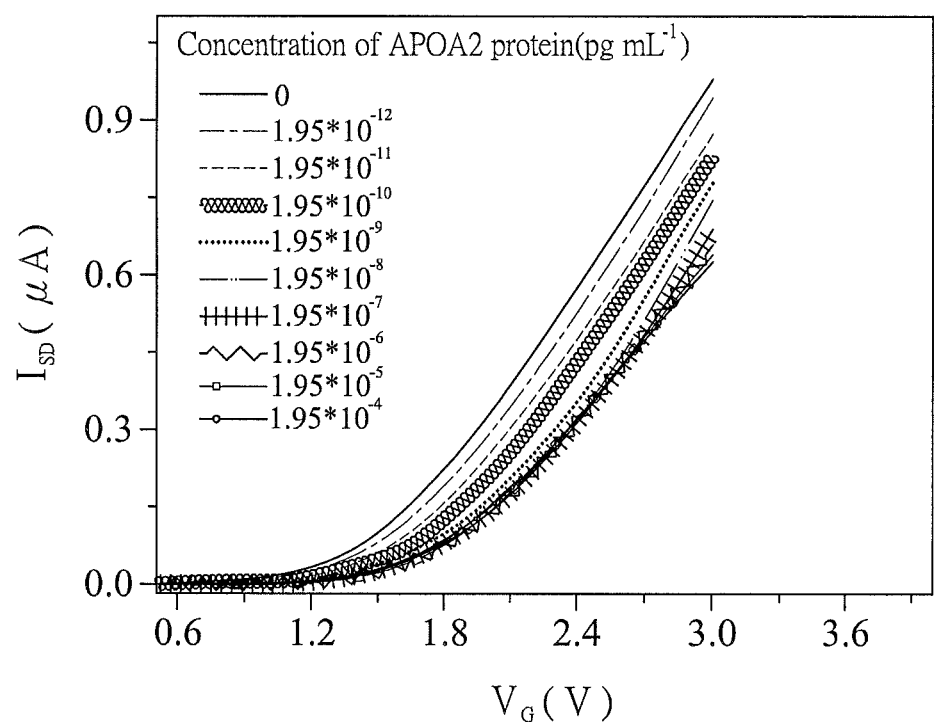
FIG. 27 is an $I_{SD}$-$V_G$ curve plot illustrating current changes of the biosensor (Ab-MGLA/poly-SiNW-FET) of Example 3 after the addition of various concentrations of the APOA2 protein.

As shown in FIG. 27, the after-reaction current at the gate voltage of 3V decreased with an increase in the concentration of the APOA2 protein due to the depletion of charge carriers in the poly-SiNW-FET, while the negatively charged protein remained bound to the Ab-MGLA surface.

Figure 28:
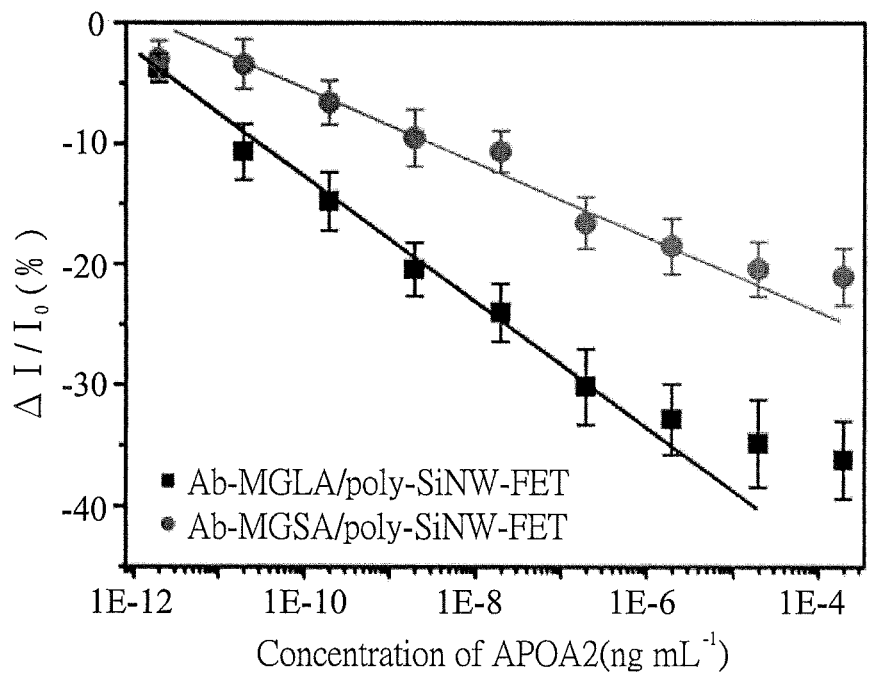
FIG. 28 is a plot illustrating the effects of the concentration of the APOA2 protein on the current changes of the biosensor (Ab-MGLA/poly-SiNW-FET) of Example 3 and the biosensor (Ab-MGSA/poly-SiNW-FET) of Comparative Example 1.

(b) Comparison of Influence of Concentration of APOA2 Protein on a Biosensor of Ab-MGLA/Poly-SiNW-FET and a Biosensor of Ab-MGSA/Poly-SiNW-FET:

The after-reaction current of the biosensor of Ab-MGSA/poly-SiNW-FET obtained in Comparative Example 1 was measured according to the aforesaid procedure after injecting solutions of APOA2 Protein in PBS at concentrations ranging from 19.5 pg/ml to 1.95 μg/ml. $\Delta I/I_0$ (%) was calculated from the after-reaction current of the biosensor (Ab-MGLA/poly-SiNW-FET) of Example 3 at a gate voltage ($V_G$) of 3V (from FIG. 27) and the after-reaction current of the biosensor (Ab-MGSA/poly-SiNW-FET) of Comparative Example 1 at a gate voltage ($V_G$) of 3V according to the aforesaid equation (IV), and was plotted versus the concentrations of the APOA2 Protein. The results are shown in FIG. 28 (n=5). The slopes of the current calibration lines corresponding to the biosensors of Example 3 and Comparative Example 1 are respectively calculated. Limit of detection (LOD) was calculated according to Equation (V) below. The results are shown in Table 8 below.

$$LOD = 3\sigma/S \quad \text{Equation (V):}$$

wherein

σ: standard derivation of a biosensor in a pure buffer (PBS); and

S: slope of a current calibration line (i.e., sensitivity) of a biosensor at low concentration of APOA2 Protein.

TABLE 8

|  | LOD (pg/mL) |
|---|---|
| Ex. 3 | 6.7 |
| Comp. Ex. 1 | 95.9 |

As shown in FIG. 28, compared to the biosensor of Ab-MGLA/poly-SiNW-FET, the biosensor of Ab-MGSA/poly-SiNW-FET exhibited a linear dependence of relative response on the logarithmical concentration in a range from 195 pg/ml to 19.5 µg/mi, with a lower slope that corresponded to lower sensitivity.

In addition, as shown in Table 8, the value of OLD for the biosensor of Example 3 is significantly lower than that for the biosensor of Comparative Example 1, which indicates that the biosensor of Example 3 has enhanced antibody bioactivity. The superior performance of the biosensor of Example 3 can be attributed to the higher amount of bioactive sites and lower steric hindrance with respect to protein binding.

Notably, in the aforesaid examples, the scan range was from 0 to 3 V at a scan rate of 0.5 V/s, resulting in a response time of 6 s, which indicates that the biosensor of the disclosure has the characteristic of short response time.

Analysis of Stability of a Biosensor:

The biosensors obtained in Examples 1-4 may be stored in a dry environment at 4° C. for one week. The relative currents for 1 ng/ml of the APOA2 protein decreased by approximately 20.2% for the biosensor of Ab-MGLA/poly-SiNW-FET obtained in Example 3 and 19.5% for the biosensor of Ab-MGSA/poly-SiNW-FET obtained in Comparative Example 1 after one week of storage, as compared to the values obtained for fresh biosensors. It has thus been demonstrated that the biosensor of this disclosure may be stored stably.

Figure 29:
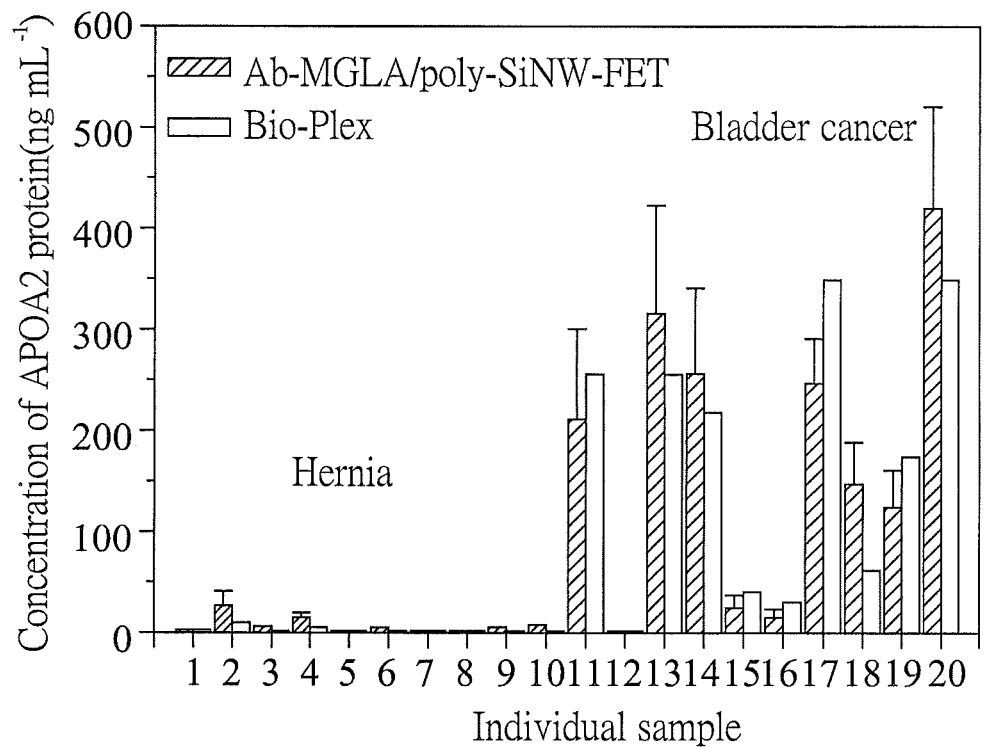
FIG. 29 is a bar chart illustrating APOA2 protein concentrations in urine samples from hernia and bladder cancer patients using the biosensor (Ab-MGLA/poly-SiNW-FET) of Example 3 and a Bio-Plex assay.

Determination of Concentration of APOA2 Protein in Human Urine from Hernia Patients and Bladder Cancer Patients using Bio-Plex and a Biosensor of Ab-MGLA/poly-SiNW-FET:

20 urine samples were collected, in which 10 urine samples were collected from hernia patients (as controls) and 10 urine samples were collected from bladder cancer patients. The concentration of the APOA2 protein in each of the urine samples was measured using a Bio-Plex and the biosensor of Example 3. The results are shown in FIG. 29 (n=3). The urine samples were collected by a process descried in the aforesaid "Collection of Clinical Urinary Specimen" section. The determination of the concentration of the APOA2 protein in each of the urine samples with the biosensor of Example 3 was performed using 5 µl of each of the urine samples and using a bias voltage ($V_B$) of 50-mV.

As shown in FIG. 29, in the urine samples of hernia patients, the concentration of the APOA2 protein is 0.425-9.47 ng/ml, which is significantly lower than the concentration of the APOA2 protein of 29-344 ng/ml that is typically observed in patients suffering from late- and advanced-stage bladder cancer. These results demonstrate that the Ab-MGLA/poly-SiNW-FET biosensor of this disclosure can be used to distinguish the protein levels in hernia and bladder cancer patients. The results measured by the biosensor of the disclosure are also in agreement with those measured by the Bio-Plex system, which indicates that the diagnosis of bladder cancer based on the Ab-MGLA/poly-SiNM-FET biosensor of the disclosure is feasible and accurate and that the assay using the biosensor of the disclosure is less complex and time-consuming than the Bio-Plex system. In addition, compared to cystoscopy, the Ab-MGLA/poly-SiNM-FET biosensor of the disclosure is non-invasive and can reduce patient pain and discomfort.

While the disclosure has been described in connection with what are considered the exemplary embodiments, it is understood that this disclosure is not limited to the disclosed embodiments but is intended to cover various arrangements included within the spirit and scope of the broadest interpretation so as to encompass all such modifications and equivalent arrangements.

The invention claimed is:

1. A reduced graphene oxide-based biosensor comprising a nano-structure field-effect transistor, said transistor including a channel region that contains a composite formed of (i) a reduced graphene oxide having a linking moiety of the formula —(C=O)—X—COOH, X being a $C_2$-$C_3$ alkenylene group or a $C_1$-$C_3$ alkylene group, bonded to an antibody specific to an analyte; and (ii) a magnetic nanoparticle adsorbed onto said reduced graphene oxide.

2. The reduced graphene oxide-based biosensor according to claim 1, wherein said channel region further contains an immobilization layer for immobilizing said composite.

3. The reduced graphene oxide-based biosensor according to claim 1, wherein X is a $C_2$-$C_3$ alkenylene group.

4. The reduced graphene oxide-based biosensor according to claim 3, wherein X is a vinylene group.

5. The reduced graphene oxide-based biosensor according to claim 1, wherein said nano-structure field-effect transistor is a polycrystalline silicon nanowire field-effect transistor.

6. The reduced graphene oxide-based biosensor according to claim 1, wherein said antibody is an anti-APOA2 antibody.

7. The reduced graphene oxide-based biosensor according to claim 1, wherein said magnetic nanoparticle is selected from a group consisting of a $Fe_3O_4$ magnetic nanoparticle, a Ni magnetic nanoparticle, and a combination thereof.

8. The reduced graphene oxide-based biosensor according to claim 1, wherein said composite has a size ranging from 30 nm to 50 nm.

9. The reduced graphene oxide-based biosensor according to claim 2, wherein said immobilizing layer is made by forming a self-assembled monolayer of an aminosilane compound in said channel region, and reacting said self-assembled monolayer with a dialdehyde compound to attach an aldehyde group of said dialdehyde compound to said self-assembled monolayer.

10. The reduced graphene oxide-based biosensor according to claim 1, wherein said reduced graphene oxide having said linking moiety is made by subjecting a cyclic dianhydride compound and a graphite to a Friedel-Crafts reaction in the presence of a Lewis acid.

11. A method for detecting an analyte using the reduced graphene oxide-based biosensor according to claim 1, comprising the steps of: applying a predetermined potential to a channel region through a gate electrode of the reduced graphene oxide-based biosensor; bringing the reduced graphene oxide-based biosensor into contact with the analyte; and measuring a change in current of the reduced graphene oxide-based biosensor before and after the reduced graphene oxide-based biosensor is brought with contact with the analyte for determining a concentration of the analyte.

* * * * *